(12) United States Patent
Lefenfeld et al.

(10) Patent No.: US 8,759,599 B2
(45) Date of Patent: Jun. 24, 2014

(54) CATALYTIC DEHYDRATION OF ALCOHOLS USING PHASE PURE, CALCINED SINGLE- AND MULTI-SITE HETEROGENEOUS CATALYSTS

(75) Inventors: Michael Lefenfeld, New York, NY (US);
Robert Raja, Eastleigh (GB);
Alexander James Paterson, Perth (GB);
Matthew Edward Potter, Southhampton (GB)

(73) Assignee: Signa Chemistry, Inc., New York, NY (US)

( * ) Notice: Subject to any disclaimer, the term of this patent is extended or adjusted under 35 U.S.C. 154(b) by 646 days.

(21) Appl. No.: 12/692,561

(22) Filed: Jan. 22, 2010

(65) Prior Publication Data

US 2010/0249476 A1 Sep. 30, 2010

Related U.S. Application Data

(60) Provisional application No. 61/146,844, filed on Jan. 23, 2009.

(51) Int. Cl.
*C01B 25/36* (2006.01)
*C07C 5/02* (2006.01)

(52) U.S. Cl.
USPC ............................ 585/632; 423/306; 585/627

(58) Field of Classification Search
USPC ................................... 423/306; 585/627, 632
See application file for complete search history.

(56) References Cited

U.S. PATENT DOCUMENTS

| | | |
|---|---|---|
| 4,134,926 A | 1/1979 | Tsao et al. |
| 4,351,732 A | 9/1982 | Psaras et al. |
| 4,423,270 A | 12/1983 | Pearson |
| 4,499,327 A | 2/1985 | Kaiser |
| 4,556,460 A | 12/1985 | Robertson et al. |

(Continued)

FOREIGN PATENT DOCUMENTS

| | | |
|---|---|---|
| EP | 0 141 662 A2 | 5/1985 |
| EP | 1142833 A1 | 10/2001 |

(Continued)

OTHER PUBLICATIONS

Wong et al. "Isomorphous Substitution of Iron into Aluminophosphate Molecular Sieve, AlPO4-5" 1992 Journal of catalysis, 133, 159-169.*

(Continued)

*Primary Examiner* — Wayne Langel
*Assistant Examiner* — Syed Iqbal
(74) *Attorney, Agent, or Firm* — J.A. Lindeman & Co., PLLC

(57) ABSTRACT

The disclosure describes a new class of isomorphously metal-substituted aluminophosphate materials with high phase purity that are capable of performing selective Brönsted acid catalyzed chemical transformations, such as transforming alcohols to olefins, with high conversions and selectivities using mild conditions. Isomorphous substitutions of functional metal ions for both the aluminum ions and the phosphorous ions were successful in various AlPO structures, along with multiple metal substitutions into a single aluminum site and/or a phosphorous site. This invention can be used towards the catalytic conversion of hydroxylated compounds of linear and/or branched moiety with the possibility of being substituted to their respective hydrocarbon products, preferably light olefins containing 2 to 10 carbon atoms, among other chemistries.

26 Claims, 5 Drawing Sheets

(56) References Cited

U.S. PATENT DOCUMENTS

| | | | |
|---|---|---|---|
| 4,605,492 | A | 8/1986 | Lok et al. |
| 4,677,243 | A | 6/1987 | Kaiser |
| 4,704,478 | A | 11/1987 | Olson |
| 4,752,651 | A | 6/1988 | Kaiser |
| 4,822,478 | A * | 4/1989 | Lok et al. .................. 208/111.35 |
| 5,141,729 | A | 8/1992 | Chang et al. |
| 5,478,787 | A * | 12/1995 | Dandekar et al. ............... 502/66 |
| 5,952,538 | A | 9/1999 | Vaughn et al. |
| 6,046,673 | A | 4/2000 | Michael et al. |
| 6,294,493 | B1 * | 9/2001 | Strohmaier et al. ............ 502/64 |
| 6,334,994 | B1 | 1/2002 | Wendelbo et al. |
| 6,540,970 | B1 | 4/2003 | Strohmaier et al. |
| 6,936,566 | B2 | 8/2005 | Mees et al. |
| 7,199,277 | B2 | 4/2007 | Xu et al. |
| 7,626,067 | B2 | 12/2009 | VanEgmond et al. |
| 2006/0149109 | A1 | 7/2006 | Ruziska et al. |

FOREIGN PATENT DOCUMENTS

| | | |
|---|---|---|
| WO | WO 93/024430 | 12/1993 |
| WO | WO 03/000412 A1 | 1/2003 |
| WO | WO 03/000413 A1 | 1/2003 |
| WO | WO03035549 | 1/2003 |
| WO | WO 2005/046867 A1 | 5/2005 |
| WO | WO 2007/032899 A2 | 3/2007 |
| WO | WO 2007/083241 A2 | 7/2007 |

OTHER PUBLICATIONS

Deng et al. "Substitution of Aluminum in Aluminophosphate Molecular Sieve by Magnesium: A Combined NMR and XRD Study" 1995, vol. 99 No. 16 p. 6029-6035.*
M. Ladisch et al., *Science*, vol. 205, pp. 898-900, Aug. 31, 1979.
Kirk-Othmer Encyclopedia of Chemical Technology, Index to vols. 1-26, $5^{th}$ ed. Wiley (2004-2007).
Ullmann's Encyclopedia of industrial Chemistry, $6^{th}$ ed. Wiley (2003).
S. Golay et al., "Influence of the catalyst acid/base properties on the catalytic ethanol dehydration under steady state and dynamic conditions. In situ surface and gas-phase analysis", Chem. Eng. Sci. 54 (1999) pp. 3593-3598.
Geissman, T.A., "Principles of Organic Chemistry", 4th ed, W.H. Freeman & Co. San Francisco, ( 1977).
Morrison et al., "Organic Chemistry", 3rd ed., Allyn & Bacon (1973).
Allinger et al., "Organic Chemistry", Worth Publishers, Inc. (1971).
M Zahedi-Niaki et al., "H2O2 oxidation and epoxidation of hydrocarbons and alcohols over titanium aluminophosphates TAPO-5, TAPO-11, and TAPO-36", Journal of Catalysis, vol. 177, No. 2, Jul. 25, 1998, pp. 231-239.
Rosemarie Szostak, "Handbook of Molecular Sieves," Jan. 15, 1992, Springer, pp., 31-33, 295, 298-299, 322-326, 408-411, 416-417, 467, 492, 494, 507-509.
Supplementary European Search Report, for corresponding EP application No. 10733948.3; issued Dec. 13, 2012, 10 pages.

* cited by examiner

Powder XRD spectra of MgZnSiAlPO-5 (top), ZnSiAlPO-5 (middle) and ZnAlPO-5 (bottom).

(A)

(B)

Kinetics for dehydration of ethanol at 453 K using Si$^{IV}$AlPO-5

Kinetics for dehydration of ethanol at 463 K using Mg$^{II}$AlPO-5

Kinetics for dehydration of ethanol at 453 K using $Mg^{II}Si^{IV}AlPO-5$

Kinetics for dehydration of ethanol at 483 K using $Mg^{II}Si^{IV}AlPO-5$

CATALYTIC DEHYDRATION OF ALCOHOLS USING PHASE PURE, CALCINED SINGLE- AND MULTI-SITE HETEROGENEOUS CATALYSTS

CROSS-REFERENCE TO RELATED APPLICATIONS

This application claims priority to U.S. Provisional Application 61/146,844, filed Jan. 23, 2009, which is incorporated herein by reference.

FIELD OF THE INVENTION

This invention relates to new aluminophosphate (AlPO or $AlPO_4$) catalysts with isomorphous substitutions for the aluminum ($Al^{III}$) and/or the phosphorus ($P^V$) ions to form strong Brönsted acid sites within a single catalyst. Also, multiple metal ion isomorphous substitutions can be made for both the aluminum ($Al^{III}$) and the phosphorus ($P^V$) ions in the same instance—generating no fewer than two different acid sites. The catalysts can be used in acid-catalyzed reactions, such as the dehydration of numerous oxygenated compounds to form their respective olefin.

BACKGROUND OF THE INVENTION

Olefins and their substituted counterparts (defined herein as, but not limited to, ethylene, propylene, butenes, and mixtures thereof) serve as feedstocks for the production of numerous chemicals and polymers. For example, ethylene is one of the largest volume chemical intermediates in the world, being used as a raw material in the production of, for example, polyethylene, ethylbenzene-styrene, ethylene dichloride, ethylene oxide and ethylene glycol. Most olefins are commercially produced by the thermal or catalytic cracking of saturated hydrocarbons found in petroleum and naphtha (See M. Ladisch et al., *Science* (1979) 205, 898). Due to the thermodynamic limitations of the reaction, thermal cracking reactors operate at temperatures as high as 1,100° C. to maintain the desired levels of conversion—typical yields are between 50 and 100% (See U.S. patent applications and patents: 2006/0149109; U.S. Pat. Nos. 4,351,732; 4,556,460; 4,423,270; and 4,134,926). Information on production of ethylene by thermal cracking is available in *Kirk Othmer Encyclopedia of Chemical Technology*, 5$^{th}$ ed. Wiley (2004-2007) and *Ullmann's Encyclopedia of Industrial Chemistry*, 6$^{th}$ ed. Wiley (2003), both hereby incorporated by reference.

Finding new, more efficient, and environmentally friendly pathways to produce olefins from renewable starting materials that are not encumbered by the varying costs and tightening supply of crude petroleum has been a challenging research area of the past decade (See U.S. patent applications and patents: 2006/0149109; U.S. Pat. Nos. 4,351,732; 4,556,460; 4,423,270; and 4,134,926). Catalytic oxidative dehydration of ethane was proposed as an alternative method to produce ethylene at much lower temperatures, but the yields and selectivity achieved to date have not been encouraging (See S. Golay et al., *Chem. Eng. Sci.* (1999) 54, 3593).

Dehydration of oxygenates are conventionally carried out using either concentrated sulfuric acid or concentrated phosphoric acid, $H_3PO_4$. The mechanistic details for the dehydration reaction can be summarized in Scheme 1 (below). The alcohol is first protonated, followed by a loss of water to give a carbocation (carbonium ion), which results in the subsequent abstraction of a hydrogen ion from the carbocation. Apart from the acid's corrosive nature, as a side reaction, the acid can oxidize the alcohol into polluting carbon dioxide. Also, in the case of concentrated $H_2SO_4$, large quantities of sulfur dioxide can be produced. Both of these gases have to be removed from the product olefin before it can be used in a later chemical process.

Scheme 1. Mechanism for the Acidic Dehydration of Alcohols

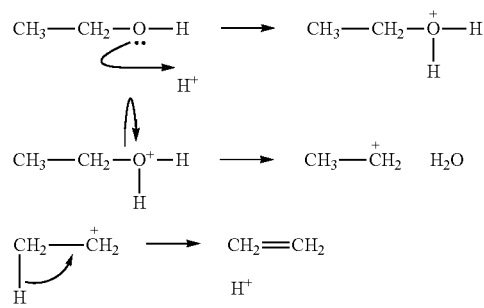

Silicoaluminophosphates (SAPOs), such as SAPO-34 and its analogues, possess strong Brönsted acid sites and are excellent shape-selective catalysts for the conversion of methanol and other alcohols to light olefins (See U.S. Pat. Nos. 4,499,327; 5,952,538; 6,046,673; 6,334,994; and 7,199,277; as well as WO 1993/024430). However, SAPOs are composed of Si atoms tetrahedrally coordinated to oxygen atoms making an integral part of the overall catalyst framework. SAPO-34 is being commercially exploited (by UOP) for the selective conversion of methanol to low-molecular weight olefins (See WO 2007/032899). Further, the Brönsted acidity of a SAPO varies greatly depending on its particular structure type and architecture.

To vary the intensity and number of Brönsted acid sites in aluminophosphates (AlPOs), one can isomorphously introduce ions to replace a portion of the $Al^{III}$ ions with a single type of divalent metal ion, such as Zn, Mg, Mn, Co, Ni, Cu, and Fe, among others. In other words, a fraction of the $\equiv Al^{III}$—O—$P^V\equiv$ linkages is replaced by $\equiv M^{II}$-O(H)—$P^V\equiv$, the proton that is loosely attached to the bridging oxygen being the locus of the Brönsted acid center. The properties of the resulting Brönsted acid center can be controlled by the appropriate choice of structure-directing agents, transition-metal precursor, or gel composition, leading to a wide range of solid-acid catalysts. However, by substituting only the $Al^{III}$ ion or the $P^V$ ion in the framework, only partial tuning of the acid strength occurs. See, for example, EP0141662A2. Yet, phase purity must also be accomplished to get significant selectivity towards the desired product of the reaction.

Olefins, particularly light olefins, are the most desirable products from oxygenate conversion and crude petroleum cracking. A need exists to improve the performance of ethylene plants. To this end, a number of catalytically mediated processes have been proposed. The most chemically straightforward among these is ethanol dehydration. This invention meets that need and provides the full tuning of the AlPO acid strength via controlled, judicious, and simultaneous substitution of both the $Al^{III}$ and $P^V$ ions combined with substantial phase purity of the calcined catalyst.

SUMMARY OF THE INVENTION

The invention relates to a new class of three-dimensional crystalline isomorphously metal-substituted aluminophosphate materials with high phase purity that are capable of performing selective Brönsted acid catalyzed chemical transformations, such as transforming alcohols to olefins, with high conversions and selectivities using mild conditions. Isomorphous substitutions of functional metal ions for both the aluminum ions and the phosphorous ions were successful in various AlPO structures, along with multiple metal substitutions into a single aluminum site and/or a phosphorous site and with substantial phase purity of the substituted AlPO after calcining. The AlPO compositions of this invention can be used in the catalytic conversion of hydroxylated compounds of linear and/or branched alkyl or aralkyl moiety with the possibility of being substituted to their respective hydrocarbon products, such as, for example, light olefins containing 2 to 10 carbon atoms, among other chemistries. Advantageously, the process of the invention may take place with the hydroxylated compound in the liquid phase.

DETAILED DESCRIPTION OF THE INVENTION

Figure 1:
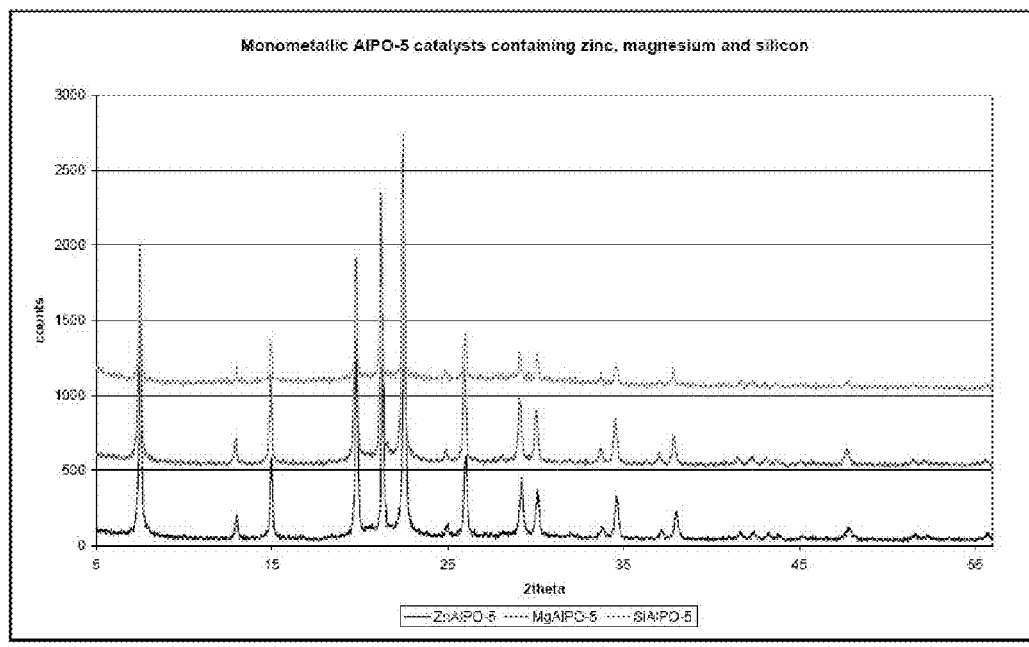
FIG. 1 is an X-ray Diffraction Pattern of 3 different isomorphously substituted mono-metallic AlPO-5s ($Mg^{III}$, $Zn^{II}$, and $Si^{IV}$) showing they are phase pure and crystalline.

Processes for converting alcohols to olefins via dehydration are known in the art. The invention relates to new catalysts and their use in the dehydration of light alcohols (also described in the art as hydroxylated compounds or oxygenates) to form their respective light olefins. The process relates to making light olefins containing 2 to 10 carbon atoms from oxygenates wherein said process comprises contacting a feedstock containing an alcohol (an oxygenate feedstock) with an isomorphously, metal-substituted aluminophosphate (AlPO) catalyst of the invention comprising a molecular framework of [$AlO_2^-$] and [$PO_2^+$] tetrahedral units, at effective process conditions to produce such light olefin products. As used herein, the isomorphously, metal-substituted aluminophosphate (AlPO) catalysts of the invention refer to a substantially phase-pure, calcined aluminophosphate, $AlPO_4$, where at least one aluminum ($Al^{III}$) site is isomorphously metal-substituted by a divalent metal ion ($M^{II}$) and/or at least one phosphorous ($P^V$) site is isomorphously metal-substituted by a tetravalent metal ion ($M^{IV}$).

The terms "light alcohols" or "light olefins" refers to alcohols and olefins having two to ten carbon atoms, inclusive. Although other hydrocarbon products are formed, the products of particular interest herein are the light olefins and they are preferably produced as the major hydrocarbon products i.e., over 50 mole percent of the hydrocarbon product is light olefins. The ability of the isomorphously metal-substituted AlPO catalysts of the invention to catalytically provide for the formation of light olefins from alcohols in the liquid phase, preferably as the major portion of the hydrocarbon product, has not heretofore been reported or suggested. Examples of alcohol dehydration include: conversion of lower alkanols to their corresponding olefins, especially ethanol to ethylene, propanol to propylene, t-butyl alcohol to isobutylene, and methyl benzyl alcohol to styrene.

Isomorphously Metal-Substituted Aluminophosphate (AlPO) Catalyst Preparation and Composition The invention relates to new aluminophosphate catalysts ($AlPO_4$ or AlPOs) with isomorphous substitutions for the aluminum ($Al^{III}$) and the phosphorus ($P^V$) ions at both atom positions at the same time, to form strong and tunable Brönsted acid sites within a single catalyst. Also, isomorphous substitutions for multiple metal atoms can be made for either the aluminum or the phosphorus ions alone (incorporating as few as two new and different strength acid sites) as well as for both $Al^{III}$ and $P^V$ in the same instance. These three-dimensional catalysts comprise a stable crystalline solid framework enclosing cavities of multi-Ångstrom diameter. The cavities form a well-defined system of cages with one-, two-, and/or three-dimensional channels that can be connected to each other. The pore diameter can be as small as 3 Ångstroms and as large as 15 Ångstroms or more. Most of the chemical transformations are believed to occur inside the solid framework. Accordingly, the invention relates to isomorphously metal-substituted aluminophosphates (AlPO's). Mono-substituted AlPO's of the invention must be substantially phase pure and have at least one aluminum, ($Al^{III}$), site substituted by a divalent metal ion ($M^{II}$) or at least one phosphorous, ($P^V$), site substituted by a tetravalent metal ion ($M^{IV}$). In the mono-substituted AlPOs of the invention, the $Al^{III}$ or the $P^V$ sites may each be multiply substituted with two or more such metal ions. The invention also relates to substantially phase pure bi-substituted AlPO's where at least one aluminum, ($Al^{III}$), site is substituted by a divalent metal ion ($M^{II}$) and at least one phosphorous, ($P^V$), site is substituted by a tetravalent metal ion ($M^{IV}$). In the bi-substituted AlPOs of the invention, the $Al^{III}$ and/or the $P^V$ sites may each be multiply substituted with two or more such metal ions.

AlPOs have a three-dimensional microporous crystalline framework incorporating tetrahedral units with the designation $MO_2^n$ (where "M" is a metal or metal-like species and "n" is the net electric charge), specifically $AlO_2^-$ with $PO_2^+$ for AlPOs, with or without metals or other substituents in the complete structure. In the cases of $AlO_2^-$ and $PO_2^+$, the Al atom has a +3 charge resulting in a net charge of −1 for the unit and the P atom has a +5 charge resulting in a net charge of +1 for the unit. Of course, as known to those familiar with the art, other "M" atoms may be used and incorporated to form tetrahedral units of various net oxidation states, for example SAPOs, which has been the only method until now to encase a higher than +3 valence state.

Since the aluminophosphate (AlPO) framework is inherently neutral in electric charge, the incorporation of silicon, or other elemental, tetrahedral units into the framework through substitution generates more active catalytic sites, specifically acid sites and increased acidity, leading to enhanced selectivities. In other words, the catalyst compositions of the invention allow tuning of the Brönsted acid sites and activity within the catalyst. Until now, the only known method to incorporate silicon is through the generation of a SAPO by silicon tetrahedral unit incorporation, where the gel composition is representative of a SAPO and the primary framework is built around the Si tetrahedral unit in a stoichiometric amount. Controlling the quantity and location of silicon atoms and other elements is important in determining the catalytic properties of a particular AlPO catalyst.

Compared to mineral acids, the AlPO catalysts of the invention have the advantage of reduced corrosion and have no need to be separated from reaction products. Compared to Lewis and Brönsted acids and ion exchange resins, they are stronger acids and have better temperature stability than ion exchange resin and most Lewis and Brönsted acids. They are also stronger acids than most other heterogeneous acid catalysts.

Properly adjusted acid strength, acidity distribution, and acid site density are the keys to forming a high oxygenate conversion or petroleum cracking catalyst. This invention, for the first time, describes how the $P^V$ ion may be exchanged for a lower valence metal, like $Si^{IV}$ among other metals with similar +4 valence states, combined with a substitution of the $Al^{III}$ ion by a metal, like $Mg^{II}$ among other metals with a +2 valence state. These new substituted ions are incorporated into the AlPO framework through the isomorphous substitution of the $Al^{III}$ and $P^V$ ion to tune the acid strength with precision.

Often, the $Al^{III}$ ion is substituted to incorporate other metal ions to increase the active catalytic sites, such as adding metals of a +2 valence to generate acid sites, within the AlPO framework. The silicon ion has only been incorporated into these three-dimensional frameworks via (i) the post-synthesis route or (ii) through the art known to generate SAPOs, by adding a stoichiometric amount of silicon tetrahedral units altering the crystal structure of the starting AlPO.

In this invention, a new metal ion, which includes metals and metalloids, of lower valence, $M^{IV}$ has been substituted isomorphously into the AlPO framework by replacing the phosphorous ion, $P^V$ with cations of +3 valence to generate Brönsted acid sites simultaneously with the replacement of one or more $Al^{III}$ sites with different cations of +2 valence. $M^{IV}$ includes, but is not limited to, $Si^{IV}$, $Zr^{IV}$, $Pt^{IV}$, $Sn^{IV}$, $Ti^{IV}$, $Ge^{IV}$, $Pd^{IV}$, and mixtures thereof. The substitution of the silicon into the $P^V$ site has never been performed in conjunction with separate metal ion substitution for the aluminum ion, $Al^{III}$, with a new metal ion, which includes metals and metalloids, of lower valence, $M^{II}$. $M^{II}$ includes, but is not limited to, $Zn^{II}$, $Mg^{II}$, $Co^{II}$, $Ca^{II}$, $Ni^{II}$, $Pe^{II}$, and mixtures thereof. If a $M^{II}$ is used that can be oxidized to a higher valence number during preparation, the metal must be reduced under a reducing environment to return the metal to a +2 valence forming the Brönsted acid site. Lastly, multiple replacements of new metal ions ($M^{II}$ and/or $M^{IV}$) can be substituted for either, or both, of the $Al^{III}$ or $P^V$ ions generating no fewer than 3 separate kinds of acid sites in close proximity. The molar amount of $M^{II}$ substituted for $Al^{III}$ may range, for example, from about 0.001 to about 0.99 moles $M^{II}$, or further, for example, from about 0.01 to about 0.09 moles $M^{II}$, or further, for example, from about 0.03 to about 0.07 moles $M^{II}$. The molar amount of $M^{IV}$ substituted for $P^V$ may range from about 0.01 to about 0.99 moles $M^{IV}$, or further, for example, from about 0.05 to about 0.20 moles $M^{IV}$, or further, for example, from about 0.08 to about 0.17 moles $M^{IV}$.

The general method for preparing AlPO catalysts of the invention is shown in Scheme 2 below. To synthesize these AlPO frameworks with generated Brönsted acid sites, a known quantity of a phosphorous source ($PO_2^+$), including phosphoric acid, organic phosphates such as triethyl phosphate, and aluminophosphates, can be added to a known amount of water and be left to stir. Next, a known amount of an aluminum source ($AlO_2^-$), including aluminum alkoxides such as aluminum isopropoxide, aluminum phosphates, aluminum hydroxide, sodium aluminate, and pseudoboehmite, must be added slowly to the reaction mixture to stop its solidification. The entire solution is stirred vigorously. A desired amount of substituting metal source ($M^{II}$ and $M^{IV}$) is mixed in water. When it has fully suspended or dissolved, slowly add the solvated metal source into the above reaction mixture to isomorphously replace the $Al^{III}$ and/or $P^V$. The mixture is then stirred vigorously to homogenize for several minutes before adding a further quantity of water. Next, a measured quantity of structure directing agent (SDA) is slowly added into the stirring reaction mixture before adding a final amount of water and aging the resulting mixture, for example for about 1 minute to about 2 hours.

Once the synthesis reaction is complete, stirring should be terminated and the reaction contents should be transferred into a high pressure autoclave unit with resistant liners. The autoclave should be sealed and heated with the product for up to about 6 hours, such as, for example, between 1 and 3 hours, at a temperature ranging between 23° C. and 500° C., such as, for example, between 100° C. and 300° C. After the heating step is complete, the autoclave should be removed from the oven and quenched in cold water/ice for at least between 0 and 5 hours, such as, for example, between 10 minutes and 2 hours, before opening and filtering the catalyst product, using water to wash it. The catalyst product from the autoclave is an isomorphously, metal-substituted aluminophosphate (AlPO) catalyst product which still contains the SDA within its crystalline structure. Once the product has been dried, it is transferred to a furnace and slowly heated (approximately 3-5° C./minute) in an inert gas (e.g. nitrogen) at a calcination temperature ranging between 200° C. and 1000° C., such as, for example, between 400° C. and 700° C. and then calcined in air or another oxygen-containing gas for at least between 3 and 24 hours, such as, for example, between 8 hours and 16 hours, to calcine the catalyst. Prior to calcining in air, the product may be held at temperature under the flow of inert gas for about 5 minutes to about 3 hours, such as, for example for about 1 to about 2 hours. After calcining, the product is slowly cooled (approximately 3-5° C./minute) to room temperature. As used herein, the phrase "heated at" a certain temperature or variations thereof means that the oven, furnace, or other heating device is set at the specified temperature.

Scheme 2. Flow diagram of the general synthesis of the substituted AlPO framework

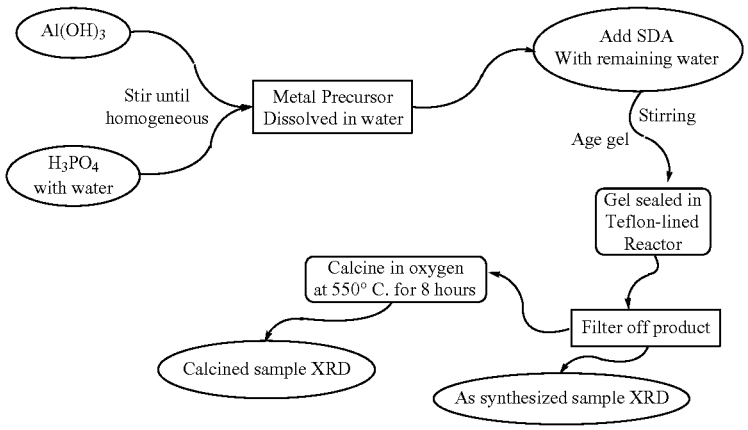

Preferred sources of Metal Precursors 1 and 2 being $M^{II}$ and $M^{IV}$ include, but are not limited to, magnesium (II) acetate, zinc (II) acetate, silica (fumed), and titanium (IV) isopropoxide, germanium (IV) methoxide, nickel (II) acetate tetrahydrate, tin chloride (IV) pentahydrate, zirconium (IV) acetate hydroxide, manganese (II) acetate, cobalt (II) acetate tetrahydrate, and copper (II) acetate monohydrate.

Preferred SDA's include, but are not limited to, tetramethylammonium (TMAOH), tetraethylammonium (TEAOH), tetrapropylammonium (TPAOH), or tetrabutylammonium ions; di-n-propylamine; tripropylamine (TPA); triethylamine (TEA); triethanolamine; piperidine; cyclohexylamine; 2-methylpyridine; N,N-dimethylbenzylamine; N,N-diethylethanolamine; dicyclohexylamine; N,N-dimethylethanolamine; choline; morpholine (MOR); N,N'-dimethylpiperazine; 1,4-diazabicyclo(2,2,2) octane; N-methyldiethanolamine, N-methylethanolamine; diisopropylethylamine (DIPE); N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentyl amine; di-n-pentylamine; isopropylamine; t-butylamine; ethyldicyclohexylamine (EDCHA); methyldicyclohexylamine (MD-CHA); ethylenediamine; pyrrolidine; and 2-imidazolidone. As will be readily apparent from the illustrative examples set forth hereinafter, not every template will produce every AlPO composition although a single template can, with proper selection of the reaction conditions, be used in the formation of different isomorphously, metal-substituted aluminophosphate (AlPO) catalysts of the invention, and a given AlPO composition can be made using different templates. As known in the art, these templates lead to various pore sizes and orientations in the framework of the specific AlPO being synthesized, which is designated by a number at the end of the AlPO name (i.e., AlPO-5).

The AlPOs of the invention display many catalytic advantages in acid-catalyzed transformations. Not least among these advantages are the catalysts' high internal surface area, which becomes accessible to reactant molecules of certain size and shape, and from which those products of appropriate dimension can diffuse. Some example AlPOs and their surface area measurement are shown below in Table 1 along with their metal content which was measured using Inductively Coupled Plasma spectroscopy (ICP). Other advantages include: (a) the ability for small quantities of isolated transition metal ions (M) to be incorporated into the AlPO frameworks; (b) relative ease of preparation, using appropriately chosen structure-directing organic templates, resulting in a considerable range of MAlPO structures differing in their micropore and cage characteristics (e.g., pore diameters, extent of pore intersection); and (c) good thermal stability. An added bonus is that, detailed quantitative knowledge about the local structure of metal-ion-centered active sites in these microporous catalysts is readily retrievable from the application of in situ techniques, such as X-ray absorption spectroscopy and FTIR.

TABLE 1

| Substituted AlPO | Empirical formula | ICP Metal content by weight/% | | | BET Surface Area $(m^2/g)$ |
| --- | --- | --- | --- | --- | --- |
| | | Mg | Zn | Si | |
| MgAlPO-5 | $Mg_{0.04}Al_{0.96}P_{1.00}O_{4.00}H_{0.04}$ | 0.81 | — | — | 193.32 |
| ZnAlPO-5 | $Zn_{0.04}Al_{0.96}P_{1.00}O_{4.00}H_{0.04}$ | — | 2.18 | — | 165.41 |
| SiAlPO-5 | $Si_{0.12}Al_{1.00}P_{0.88}O_{4.00}H_{0.12}$ | — | — | 2.66 | 181.87 |
| MgSiAlPO-5 | $Mg_{0.03}Si_{0.08}Al_{0.97}P_{0.92}O_{4.00}H_{0.11}$ | 0.58 | — | 1.93 | 167.58 |
| ZnSiAlPO-5 | $Zn_{0.03}Si_{0.04}Al_{0.97}P_{0.96}O_{4.00}H_{0.08}$ | — | 1.76 | 1.18 | 236.21 |
| MgZnAlPO-5 | $Mg_{0.04}Zn_{0.03}Al_{0.93}P_{1.00}O_{4.00}H_{0.07}$ | 0.69 | 1.84 | — | 283.78 |
| MgZnSiAlPO-5 | $Mg_{0.03}Zn_{0.03}Si_{0.17}Al_{0.94}P_{0.83}O_{4.00}H_{0.23}$ | 0.65 | 1.60 | 3.87 | 101.53 |

AlPO-5 has hexagonal symmetry with $a=1.372$ nm and $c=0.847$ nm and contains one-dimensional channels oriented parallel to the c axis that are fused by 12-membered rings composed of alternating $AlO_4$ and $PO_4$ tetrahedra. The overall framework is neutral (unlike zeolites) and the structure has distinct channels (as opposed to cages with sodalite or AlPO-18). It can be easily synthesized using a range of SDA's (e.g., triethylamine, tripropylamine, etc), as the large one-dimensional cylindrical pore system imposes fewer constraints on the template fit. This material belongs to the AFI framework type (as classified by the International Zeolite Association). The pores in this structure are formed by the alternation of squares and hexagons and have a diameter of 7.3 Å and are only 1 dimensional, thus are actually channels.

AlPO-18 is a microporous crystalline molecular sieve with a chabazite-like structure with a framework topology characterized by a three-dimensional pore system (pear-shaped) possessing 8-membered intersecting channels. The framework density (14.8 T/1000 Å°) of the AEI topology is among the lowest in the family of aluminophosphate microporous materials. AlPO-18 is typically formed using N,N-diisopropylethyl amine as the SDA and the un-substituted framework has a neutral charge.

The main difference between the AlPO-18 and AlPO-34 structures is the way in which the double six ring units are oriented. The structures are also different crystallographically, but they essentially possess a similar cage-type structure with pore openings consisting of 8-membered rings resulting in pore entry sizes of ca. 3.8 Å. While AlPO-34 belongs to the CHA framework type, AlPO-18 has an AEI-type framework.

Phase purity of the catalyst, defined herein as having only one crystalline phase, maintained through temperature and addition control, was monitored before and after calcination by a combination of powder X-ray diffraction and Reitveld analysis. The precise stoichiometry (an error of ca. $\pm 3 \times 10^{-3}$) was determined by ICP (metal) analysis. Substantial phase purity is defined as the presence or absence of certain peaks (or reflections) in the X-ray powder diffraction pattern, which permits the determination of the lattice type. Nearly all crystalline solids have a unique powder diffraction pattern in terms of the angles of reflection and their intensities. Where mixtures of compounds, or where phase impurities are present, each phase contributes to the powder diffraction pattern through its own set of reflection angles and intensities. By using the Reitveld method one can fit a calculated diffraction pattern with an experimental trace to get quantitative insights on atomic positions, which in turn provide a superior measure of the phase purity of the sample.

To ensure that a high degree of phase purity and crystallinity is achieved, the synthesis procedure, the formation of the gel, and its subsequent aging and crystallization are all carried out in Teflon vessels. The Teflon provides an inert surface with appropriate heat transfer and helps avoid the incorporation of contaminants and undesired metals, like iron, into the AlPO structure. Also, the order of material addition contributes to synthesizing superior phase pure material as at first the Al—O—P linkages, the primary and secondary building units of the AlPO, are formed followed by the isomorphous substitution of the desired metal ions into the framework. The reaction mixture must be kept homogenous and is therefore stirred at high speeds, ranging from 500 to 5,000 rpm, such as, for example, from 750 to 2,500, and further such as, for example from 1,000 to 1,500 rpm. The selection of the SDA is carried out to give a high specificity towards the desired AlPO product, for example MDCHA is a structure directing agent for AlPO-5. The choice of the appropriate SDA is critical to avoiding the co-crystallization of mixture phases or heavy phases, such as chabazite. Lastly, the amount of water used in the synthesis procedure should be sufficient to facilitate molecular homogeneity throughout the synthesis procedure, particularly of the substituting metal sources and the SDA, thereby minimizing the formation of co-crystallization of impure phases and facilitating the removal of any dense phases. Too much water may affect the crystallization of the mixture.

The calcination procedure is also significant in ensuring phase purity. The initial flow of an inert gas, such as nitrogen, during the heat ramp loosens the SDA from the tetrahedral-atom sites prior to it being removed during calcinations, which prevents any breakdown of the AlPO phase structure. The sample may also be held for a time at temperature under a flow of the inert gas. The sample is then heated under a flow of dry air gently to calcine the sample removing the SDA and any remaining water to prevent the disruption to the phase structure and crystallinity. The sample is also cooled slowly to prevent disruption to the structure.

Accordingly, the invention also relates to a process for preparing a substantially phase pure, calcined metal-substituted aluminophosphate, AlPO, wherein at least one aluminum ($Al^{III}$) site is substituted by a divalent metal ion ($M^{II}$) and/or at least one phosphorous ($P^V$) site is substituted by a tetravalent metal ion ($M^{IV}$). The process comprises the steps of:

adding a phosphorous source, such as, for example, phosphoric acid, to water to form an aqueous mixture, stirring the aqueous mixture, adding an aluminum source, such as, for example, aluminum hydroxide, to the stirred aqueous mixture to form a first reaction mixture, adding at least one aqueous solution or suspension of a $M^{II}$ metal source, a $M^{IV}$ metal source, or both to the stirred first reaction mixture, stirring the first reaction mixture containing the metal source for a time sufficient to form a homogenized mixture, optionally adding a further quantity of water to the stirred homogenized mixture, adding a SDA to the stirred homogenized mixture to form a second reaction mixture, optionally adding water, stirring the second reaction mixture until the reaction is complete to form a substituted AlPO reaction product mixture, aging the substituted AlPO reaction product mixture, autoclaving the aged substituted AlPO reaction product mixture in a high pressure autoclave unit equipped with resistant liners to a temperature ranging between about 23° C. and about 500° C. for up to about 6 hours, quenching the autoclave, filtering the autoclaved substituted AlPO reaction product mixture to recover a solid catalyst product, which is an iso-morphously, metal-substituted aluminophosphate (AlPO) catalyst product which still contains the SDA within its crystalline structure, washing the solid catalyst product with water, drying the solid catalyst product, slowly heating the dried catalyst product under a flowing inert gas at a calcination temperature ranging between about 200° C. and about 1000° C., holding the dried catalyst product under the flowing inert gas at the calcination temperature, calcining the dried catalyst product for a time of at least about 3 to about 24 hours to form a substantially phase pure, calcined metal-substituted aluminophosphate, and slowly cooling the substantially phase pure, calcined metal-substituted aluminophosphate to room temperature.

The invention also relates to a process for preparing a substantially phase pure, calcined metal-substituted aluminophosphate, AlPO, wherein at least one aluminum ($Al^{III}$) site is substituted by a divalent metal ion ($M^{II}$) and/or at least one phosphorous ($P^V$) site is substituted by a tetravalent metal ion ($M^{IV}$) comprising the steps of:

slowly heating an isomorphously, metal-substituted aluminophosphate catalyst product containing a SDA within its crystalline structure under a flowing inert gas at a calcination temperature ranging between about 200° C. and about 1000° C., holding the isomorphously, metal-substituted aluminophosphate catalyst product under the flowing inert gas at the calcination temperature, calcining the isomorphously, metal-substituted aluminophosphate catalyst product for a time of at least about 3 to about 24 hours to form a substantially phase pure, calcined metal-substituted aluminophosphate, and slowly cooling the substantially phase pure, calcined metal-substituted aluminophosphate to room temperature.

Phase purity and the crystallinity of the catalyst is an important and integral feature of this invention. It is known in the prior art that the substitution of the $Al^{III}$ site with a transition metal may lead to the generation of a catalyst with a potential for high phase purity, but this was seldom obtained. The invention achieves the simultaneous substitution of the $Al^{III}$ site and/or the $P^V$ site with Brönsted acid sites, transition metals in the +2 and +4 valence states, respectively, and yielding catalysts with high levels of phase purity and crystallinity. Catalysts with inferior levels of crystallinity, or those containing mixed phases such as chabazite and trydimite, lead to inferior catalytic performance and, more importantly, to decreased levels of selectivity for the desired olefins.

Typical XRD patterns and Reitveld analysis of substituted AlPO catalysts of the invention demonstrate the catalyst's phase-purity, crystallinity, and unit cell dimension. These XRD patterns (shown in FIGS. 1-3) show that a high level of structural phase purity and good crystallinity were obtained in all cases. Celref analysis (shown in FIG. 4) of the XRD data show an acceptable correlation between observed and theoretically calculated peaks. In most cases, a difference in the 2theta (2θ) angle of less than 0.1000° was observed. FIG. 4 shows that despite the isomorphous substitution of metals to the AlPO, the X-ray signature of the chosen AlPO is retained. This high phase purity and high degree of crystallinity drive the catalyst's exceptional ability to perform the olefin conversion while the alcohol is in the liquid phase.

Figure 5:
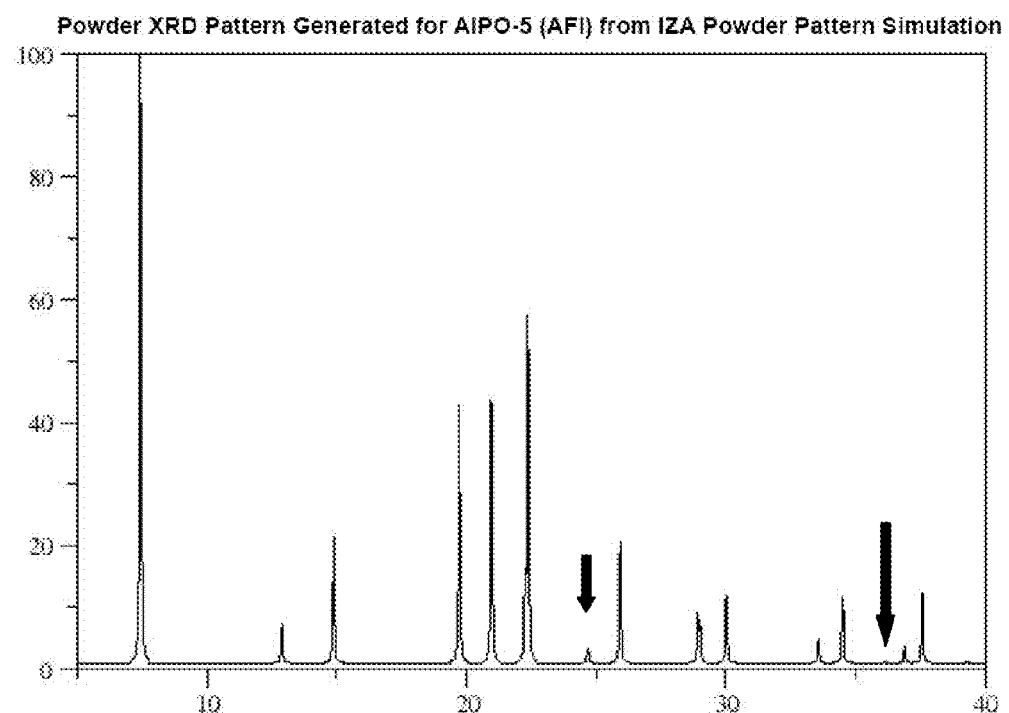
FIG. 5 (A) is the published powder x-ray diffraction (XRD) pattern generated for the AlPO-5 (AFI) from the IZA powder pattern simulation, and (B) is the overlay of the substituted AlPO-5 from EP0141662A2 Example 1 and the invented AlPO-5 Example 1 showing that the XRD from EP0141662A2 is absent of crystal plane reflections compared to FIG. 5 (A) and the pattern from the invented AlPO-5 (indicated by arrows).
Figure 5:
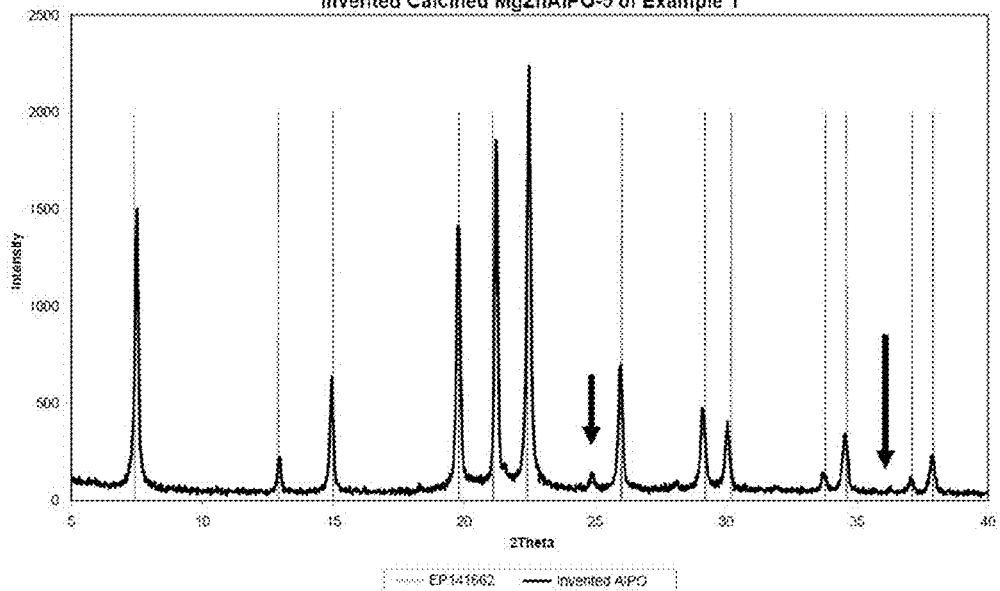
Figure 6:
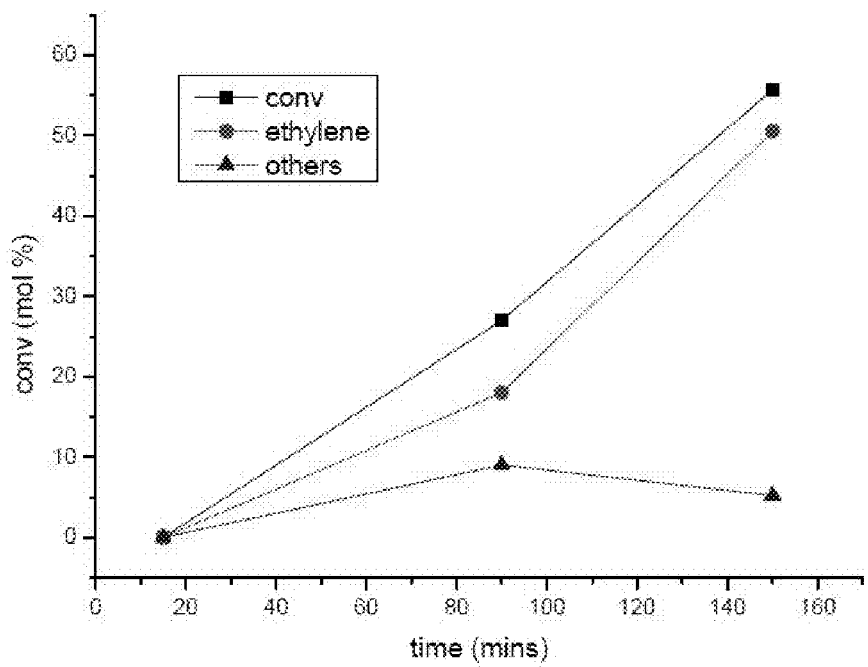
FIG. 6 is the kinetic plot showing ethanol conversion and ethylene produced versus time for the $Si^{IV}$ substituted mono-metallic AlPO-5 at 453 K.
Figure 7:
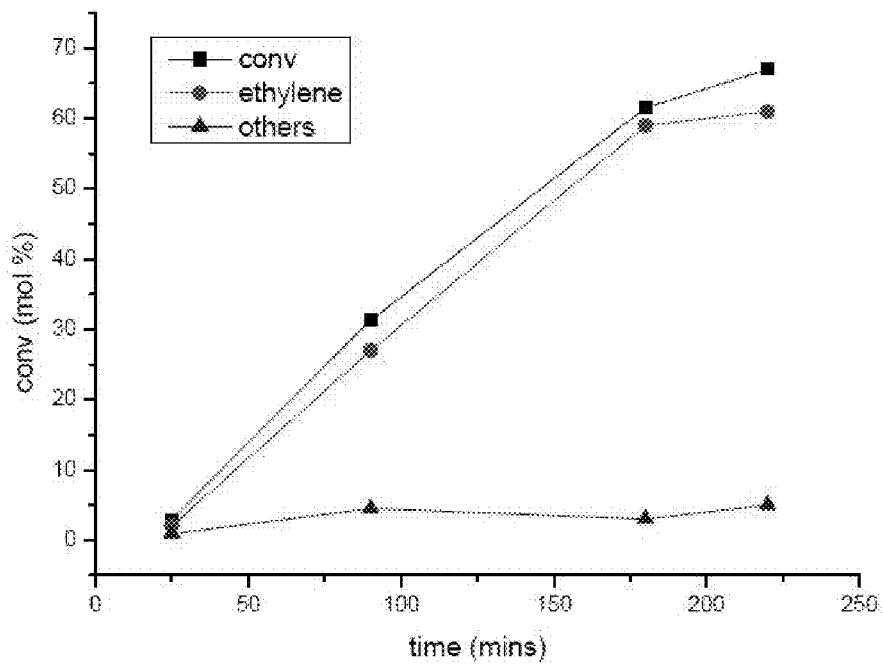
FIG. 7 is the kinetic plot showing ethanol conversion and ethylene produced versus time for the $Mg^{II}$ substituted mono-metallic AlPO-5 at 463 K.
Figure 8:
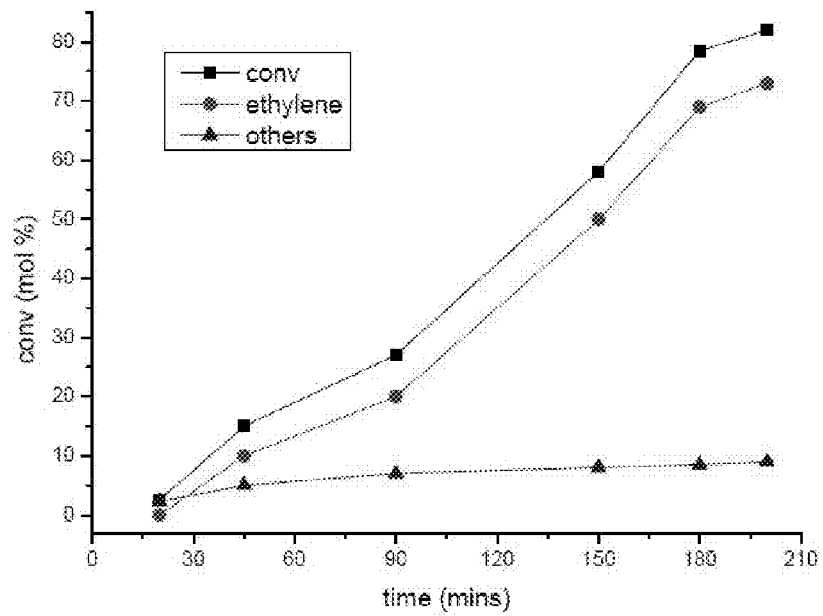
FIG. 8 is the kinetic plot showing ethanol conversion and ethylene produced versus time for the $Mg^{II}Si^{IV}$ substituted bi-metallic AlPO-5 at 453 K.
Figure 9:
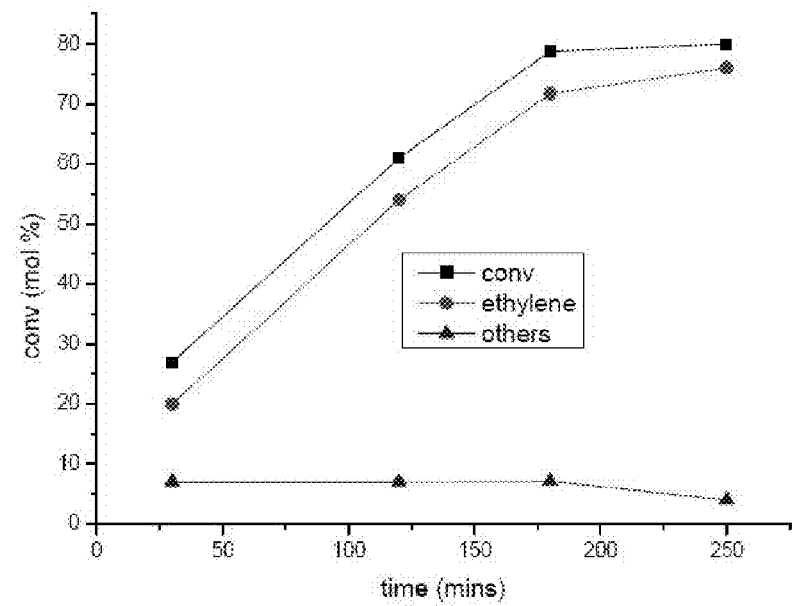
FIG. 9 is the kinetic plot showing ethanol conversion and ethylene produced versus time for the $Mg^{II}Si^{IV}$ substituted bi-metallic AlPO-5 at 483 K.

As a further demonstration of the phase purity of the AlPO compositions of the invention, FIG. 5 shows a comparison of a substituted MgZnAlPO-5 of the invention (Example 1) and a prior art substituted CoAlPO-5 from EP0141662A2, Example 1. FIG. 5 (A) is the published powder x-ray diffraction (XRD) pattern generated for the phase pure AlPO-5 (AFI) from the IZA powder pattern, simulation (http://izasc.ethz.ch/fmi/xsl/IZA-SC/mat_xrd.xsl?-db=crystal_data&-lay=web&-recid=8&-find=, Jan. 21, 2009). The XRD pattern of a phase pure AlPO-5 structure includes two peaks at 24.7 and 36.9° 2θ. FIG. 5 (B) overlays of the peak positions (vertical lines) reported for the substituted CoAlPO-5 from EP0141662A2, Example 1 and the XRD pattern for the substituted MgZnAlPO-5 of Example 2 of the invention. EP0141662A2, Example 1 lists thirteen XRD peaks each for its precalcined and calcined compositions. The XRD pattern reported for the calcined composition in EP0141662A2, Example 1 lacks two peaks at 24.7 and 36.9°θ of a phase pure AlPO-5 structure (FIG. 5 (A)). Those two peaks are either missing or substantially shifted indicating a significant change in crystalline phase or the introduction of other phases. In contrast, the XRD pattern of the substituted MgZnAlPO-5 of the invention (as indicated by the arrows) displays those two peaks, matching the XRD pattern of an AlPO-5 structure and demonstrating its phase purity.

Isomorphously Metal-Substituted Aluminophosphate (AlPO) Catalyst Uses

Metal-substituted AlPO catalysts of the invention desirably have a kinetic pore diameter such that the selectivity to the desired reaction product is greater than 50 mole percent and which permits the easy diffusion of both the reactant and the desired product. As is known in the art, the AlPO type and its corresponding pore size are determined by the SDA. The selection of the isomorphously metal-substituted AlPO catalyst for the process is preferably related, in part, to the desired product mixture sought. It is believed that the kinetic diameter of the pores of the selected metal-substituted AlPO catalyst is related to the products formed. In carrying out the dehydration of alcohols to form light olefins according to the invention, the isomorphously metal-substituted AlPO catalysts may be admixed (blended) or provided sequential to other materials which may provide some property which is beneficial under process conditions, such as improved temperature resistance or improved catalyst life by minimization of coking or which is simply inert under process conditions. Such materials may include synthetic or naturally occurring substances as well as inorganic material such as clays, silicas, aluminas, crystalline aluminosilicate zeolites, metal oxides and mixtures thereof. The relative proportions of the above materials and the isomorphously metal-substituted AlPO catalysts may vary widely ranging between about 1 and about 99 percent by weight of the composite.

In addition to the dehydration of alcohols (oxygenates) to form light olefins, discussed above, the substituted AlPO catalysts of the invention may be used for any reaction known to be catalyzed by strong acids, that include, but are not limited to, mineral acids (sulphuric acid, phosphoric acid, etc.), Lewis or Brönsted acids (aluminum chloride, etc.), ion exchange resins, as well as other heterogeneous acids. See for example, Geissman, T. A., *Principles of Organic Chemistry*, 4th ed, W.H. Freeman & Co. San Francisco, (1977), Morrison and Boyd, *Organic Chemistry*, 3rd ed., Allyn & Bacon (1973) and Allinger, N. L., et al. *Organic Chemistry*, Worth, (1971), which are incorporated herein by reference.

Preferred reactions include dehydration of alcohols to olefins, hydrolysis of olefins to alcohols, esterification, transesterification and ester hydrolysis, aldol condensation, and alkylation. Examples of alcohol dehydration include, for example: conversion of lower alkanols to their corresponding olefins, especially ethanol to ethylene, propanol to propylene, t-butyl alcohol to isobutylene and methyl benzyl alcohol to styrene. Examples of olefin hydrolysis include, for example, ethylene to ethanol and propylene to propanol.

Esterifications include, for example, the reaction of light alcohols with acids to make the corresponding esters. Examples include reaction of methanol and ethanol, respectively with acetic acid to make methyl and ethyl acetates respectively; reaction of acrylic and methacrylic acids with lower alcohols like methanol and butanol to make methyl acrylate, methyl methacrylate, and butyl methacrylate; and the reaction of 2-ethyl hexanol with phthalic anhydride to make dioctyl phthalate. An ester hydrolysis of interest includes the hydrolysis of methyl acetate to methanol and acetic acid. Transesterifications include, for example, conversion of methyl methacrylate to butyl methacrylate and conversion of alkyl glycerates to methyl esters (biodiesel) and glycerin.

Aldol condensations include, for example, reactions of aldehydes and ketones with functional aromatic compounds, including the reaction of phenol with acetone to make bisphenol A or the reaction of formaldehyde with aniline to make methylene dianiline as well as the classical self condensation of acetone to yield diacetone alcohol, mesitylene, and isophorone.

Alkylations include, for example, reactions of olefins with aromatic compounds including ethylene and benzene to ethylbenzene and propylene and benzene to cumene.

An especially preferred use for the substituted AlPO catalysts of the invention is the conversion of alcohols to olefins, such as ethanol to ethylene, where there are currently known alternative catalysts with lesser performance. In one embodiment then, the invention relates to a process for the dehydration of alcohols to form olefins. In that process, a feedstock containing an alcohol is contacted with an isomorphously metal-substituted aluminophosphate of the invention under conditions sufficient to convert the alcohol to an olefin. The alcohol is preferably a light alcohol, e.g., a $C_2$-$C_{10}$ alcohol. Examples of light chain alcohols include, but are not limited to, ethanol, propanol, butanol, pentanol, hexanol, heptanol, octanaol, nonanol, and decanol. Those having three or more carbons may be straight chains or branched, alkyl or aralkyl moiety, e.g., iso-propanol, tert-butanol, etc. The hydroxyl group may be on any carbon in the chain. The light chain alcohols may contain other substituents which do not unduly prevent or slow the dehydration reaction or poison the catalyst.

It has been discovered that by use of the newly invented metal-substituted AlPO catalysts for the conversion of such a feedstock that, in general, higher feedstock conversions and selectivities to light olefin products may be obtained as compared to that obtained by the use of the prior art unsubstituted, or monosubstituted, AlPOs and SAPOs as well as aluminosilicate zeolites as catalysts. It has also been discovered that by use of specific metal-substituted AlPO catalysts that the selectivity to $C_2$ to $C_{10}$ olefin products (e.g., ethylene, propylene, butenes, etc.) of at least about 25 mole percent, based on the total hydrocarbon products formed, may be obtained, such as, for example, in excess of 50 mole percent. Further, the selectivity to such olefin products may be in excess of 95 mole percent when specific metal-substituted AlPO catalysts of the invention are employed. In addition, it has been observed that the formation, if any, of aromatic hydrocarbons is below that which is detectable by standard vapor phase chromatographic techniques (GC). An additional bonus is that certain metal-substituted AlPO catalysts as employed in the process are believed to have increased catalyst life with respect to the conversion of the feedstock to light olefin products as compared with the crystalline aluminosilicates (ZSM-type) and unsubstituted, or monosubstituted, aluminophosphate and silicoaluminophosphate catalysts.

An alcohol to olefin conversion process of the invention can be carried out in a either a two or three phase process with the alcohol, such as ethanol, in either the liquid or vapor phase. Preferably, the reaction is carried out with the alcohol, like ethanol, in the liquid phase, such that it is contacted in a reaction zone with a solid metal-substituted aluminophosphate catalyst at effective process conditions such as to produce light olefins in the gas phase, i.e., an effective temperature, pressure, Weight Hourly Space Velocity (WHSV), and, optionally, an effective amount of diluent, correlated to produce light olefins. Maximum yield and selectivity can be achieved whether the reaction is conducted in the liquid or vapor phase making the invented catalysts superior to those known in the prior art.

The temperature that may be employed in an alcohol to olefin conversion process of the invention may vary over a wide range depending, at least in part, on the selected metal-substituted AlPO catalyst and whether the reaction is performed in the liquid or vapor phase. In general, the process can be conducted at an effective temperature ranging between about 23° C. and about 700° C. (liquid and vapor phase), such as, for example, between 50° C. and 250° C. (liquid phase) and about 250° C. and about 600° C. (vapor phase), and further such as, for example, between about 100° C. and 240° C. (liquid phase) and 300° C. and about 500° C. (vapor phase). Temperatures outside the stated range are not excluded from the scope of this invention, although such do not fall within certain desirable embodiments of the invention. At the lower end of the temperature ranges and, thus, generally at the lower rate of reaction, the formation of the desired light olefin products may become markedly slow. Notwithstanding these factors, the reaction will still occur and the feedstock, at least in part, can be converted to the desired light olefin products at temperatures Outside the ranges stated above for a process of the invention.

An alcohol to olefin conversion process of the invention is effectively carried out over a wide range of pressures including autogenous pressures. At pressures ranging between about 0.10 atmospheres and about 500 atmospheres, such as, for example, between about 1 atmosphere and about 100 atmospheres, and further such as, for example, between about 1 atmosphere and about 30 atmospheres, the formation of light olefin products will be affected although the optimum amount of product will not necessarily form at all pressures. The pressures referred to herein for the process are exclusive of the inert diluent, if any, is present, and refer to the partial pressure of the feedstock as it relates to oxygenates or mixtures thereof. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum although light olefin products can be formed An alcohol to olefin conversion process of the invention is affected for a period of time sufficient to produce the desired light olefin products. In general, the residence time employed to produce the desired product can vary from seconds to a number of hours. It will be readily appreciated by one skilled in the art that the residence time will be determined to a significant extent by the reaction temperature, the isomorphously metal-substituted AlPO selected, the WHSV, the phase (liquid or vapor) selected, and, perhaps, selected process design characteristics.

An alcohol to olefin conversion process of the invention may be carried out under process conditions comprising a temperature ranging between about 100° C. and about 240° C. (liquid phase) and 300° C. and about 500° C. (vapor phase) using a pressure ranging between about 1 atmosphere to about 30 atmospheres (liquid and vapor phase). The temperature, pressure, and WHSV are each selected such that the effective process conditions, i.e. the effective temperature, pressure, and WHSV, are employed in conjunction, i.e., correlated, with the selected metal-substituted AlPO catalyst and selected oxygenate feedstock such that light olefin products are produced.

The oxygenate feedstock is selected based on the olefin to be produced. Generally speaking, the feedstock is the corresponding alcohol (linear, branched, substituted, etc.), e.g., ethanol to produce ethylene, propanols to produce propylenes, butanols to butenes, etc. The preparation of the oxygenate feedstock is known in the art. Ideally, the feedstock should be 'dry', but especially when the reaction is carried out in the liquid phase, under conditions where the product is a gas, may contain substantial amounts of water but, of course, not so much as to adversely impact the catalytic dehydration. In addition to the presence of alcohols (e.g., ethanol, propanol, butanols, etc.), or mixtures thereof in the feedstock, a diluent may be present in the feedstock in an amount ranging between about 1 and about 99 mole percent, based on the total number of moles of all feed components fed to the reaction zone (or catalyst). Typical of the diluents which may be employed in the process are, for example, helium, argon, nitrogen, carbon monoxide, carbon dioxide, hydrogen, water (steam), paraffins, hydrocarbons (such as methane and the like), aromatics (such as benzene, toluene, xylenes and the like), mixtures thereof, and the like. Various feedstocks and their preparation as well as processes using them are described, for example, in U.S. Pat. No. 7,626,067 and published PCT applications WO 03/000412 and WO 03/000413. It has been discovered that the addition of a diluent to the feedstock prior to such being employed in the process is generally beneficial, although not required.

An alcohol to olefin conversion process of the invention may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such metal-substituted AlPO catalysts in series to provide for a desired product mixture. Owing to the nature of the process, it may be desirable to carry out the process by use of the catalyst in a dynamic (e.g., fluidized or moving) bed system or any system of a variety of transport beds rather than in a fixed bed system. Such systems would readily provide for any regeneration (if required) of the catalyst after a given period of time. If regeneration is required, the catalyst can be continuously introduced as a moving bed to a regeneration zone where it can be regenerated, such as for example by removing carbonaceous materials by oxidation in an oxygen-containing atmosphere In the preferred practice of the invention, if coking occurs, the catalyst will be subject to a regeneration step by burning off carbonaceous deposits accumulated during reactions.

The ability to carry out a three phase reaction is often advantageous. This is particularly so with reactions being carried out at conditions where the equilibrium conversion is less than 100%. It is particularly preferred to carry out the dehydration of light alcohols in a three phase system. Another group of reactions that can benefit from being practiced in a three phase system are esterifications, ester hydrolysis and transesterifications. In all of these systems the advantage of three phase operation lies in the ability to drive otherwise equilibrium limited reactions by volatilizing one or more of the products.

Three phase reactions may be carried out in any type of convenient equipment: a simple boiling reactor with the invented AlPO in the slurry phase, a trickle bed reactor (either massive or with the AlPO catalyst deployed in tubes) or even a distillation column. In the latter case, the AlPO may function as the distillation packing or may be present in discrete reaction zones within the distillation and be applied in combination with trays or other distillation packing.

EXAMPLES

Specific examples of the preparation of metal-substituted AlPO catalysts of the invention were done using the method described above. Examples 1-31 describe the reagents and conditions used to prepare the specific catalyst. RMM is defined as the sum of all relative atomic masses of the atoms in the molecule described. Examples 33 and 34 describe the catalytic dehydration of ethanol and propanol using those catalysts.

Example 1

Procedure for Making a Mono-Metallic Substituted AlPO

Synthesis of $Mg^{II}Zn^{II}AlPO$-5.

Phosphoric acid (9.601 g, 85 wt % aqueous solution, Aldrich) was diluted with $H_2O$ (10 g) in a Teflon beaker and stirred for 5 minutes. Teflon was used because the reaction vessel should be inert to the leaching of undesired metals, such as iron, into the AlPO structure. Aluminium hydroxide (4.071 g, 52.225 mmol, $Al(OH)_3.H_2O$, Aldrich) was added slowly to the beaker and stirred at high speed (between 1000 and 1,200 rpm) for 10 minutes. Magnesium acetate tetrahydrate (0.357 g, 1.668 mmol, $Mg(C_2H_3OO)_2.4H_2O$, Aldrich, 99%) and zinc acetate (0.306 g, 1.667 mmol, $Zn(C_2H_3OO)_2$, Aldrich, 99%) were measured into separate glass beakers and dissolved in 10 g of $H_2O$ each. The diluted metal precursors were then added dropwise simultaneously to the Teflon beaker. The mixture was allowed to stir at high speed (between 1000 and 1200 rpm) for 30 minutes before the SDA, methyldicyclohexylamine (MDCHA), (8.682 g, 44.443 mmol, Aldrich) was added dropwise to the mixture. The remaining water (18.17 g) was then added achieving a total 50 moles of water, maintaining substantial phase purity to avoid heavy, or dense, phase impurity formation, like chabazite. The composition of the gel was 0.94Al:1.5P:0.03Zn:0.03Mg:0.8SDA:50H$_2$O. The resulting gel was aged for 25 minutes before being transferred to Teflon-lined tubes inside stainless steel autoclaves. Teflon lined autoclaves are important for phase purity as glass or metal autoclaves with no lining lead to phase impurity formation. The sealed autoclaves were heated under autogenous pressure under static conditions in a conventional oven at 180° C. for 2 hours. The autoclaves were quenched with cold water and the resulting product was filtered, washed with water, and dried gently at 90° C.

Calcination was carried out in a tube furnace (Lenton) heated at 3° C./minute under a steady nitrogen flow until the temperature reached 550° C. The sample was then held under the nitrogen flow for 2 hours. After 2 hours the gas was changed to dry air and the sample was held under a constant gentle flow of air for 12 hours at 550° C. before being allowed to cool gently at a rate of approximately 5° C./minute to room temperature.

Example 2

Procedure for Making a Bi-Metallic Substituted AlPO

Synthesis of $Mg^{II}Zn^{II}Si^{IV}AlPO$-5.

Phosphoric acid (5.441 g, 85 wt % aqueous solution, Aldrich) was diluted with $H_2O$ (10 g) in a Teflon beaker and stirred for 5 minutes. Teflon was used because the reaction vessel should be inert to the leaching of undesired metals, such as iron, into the AlPO structure. Aluminium hydroxide (4.331 g, 55.56 mmol, $Al(OH)_3.H_2O$, Aldrich) was added slowly to the beaker and stirred at high speed (between 1,000 and 1,200 rpm) for 10 minutes. Magnesium acetate tetrahydrate (0.357 g, 1.668 mmol, $Mg(C_2H_3OO)_2.4H_2O$, Aldrich, 99%) and zinc acetate (0.306 g, 1.668 mmol, $Zn(C_2H_3OO)_2$, Aldrich, 99%) were measured into separate glass beakers and dissolved in 10 g of $H_2O$ each. The diluted metal precursors were then added dropwise simultaneously with dry fumed silica (0.677 g, 11.117 mmol, Aldrich) to the Teflon beaker. The mixture was allowed to stir at high speed (between 1000 and 1200 rpm) for 30 minutes before the SDA, methyldicyclohexylamine (MDCHA), (8.682 g, 44.443 mmol, Aldrich) was added dropwise to the mixture. The remaining water (38.92 g) was then added achieving a total 70 moles of water, maintaining substantial phase purity to avoid heavy, or dense, phase impurity formation, like chabazite. The composition of the gel was 1.00Al:0.85P:0.03Zn:0.03Mg:0.20Si:0.8SDA:70H$_2$O. The resulting gel was aged for 25 minutes before being transferred to Teflon-lined tubes inside stainless steel autoclaves. Teflon lined autoclaves are important for phase purity as glass or metal autoclaves with no lining lead to phase impurity formation. The sealed autoclaves were heated under autogenous pressure under static conditions in a conventional oven at 180° C. for 2 hours. The autoclaves were quenched with cold water and the resulting product was filtered, washed with water, and dried gently at 90° C.

Calcination was carried out in a tube furnace (Lenton) heated at 3° C./minute under a steady nitrogen flow until the temperature reached 550° C. The sample was then held under the nitrogen flow for 2 hours. After 2 hours the gas was changed to dry air and the sample was held under a constant gentle flow of air for 12 hours at 550° C. before being allowed to cool gently at a rate of approximately 5° C./minute to room temperature.

Example 3

Zn$^{II}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.0292 | 0 | |
| H$_3$PO$_4$ (85%) | 7.234 | 97.93 | 0.0627 | 1.133 | 2.9% | 0 | 190 |
| Silica | 0 | 60.09 | 0 | 0.000 | | | |
| Mg acetate•4H$_2$O | 0 | 214.46 | 0 | 0.000 | | | |
| Zn Acetate | 0.306 | 183.46 | 0.0016 | 0.030 | | | |
| MDCHA | 8.5 | 195.35 | 0.0435 | 0.785 | | | |
| H$_2$O | 70 | 18 | 3.8888 | 70.155 | | | |

Example 4

Mg$^{II}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.0291 | 0 | |
| H$_3$PO$_4$ (85%) | 7.112 | 97.93 | 0.0617 | 1.114 | 2.9% | 0 | 200 |
| Silica | 0 | 60.09 | 0 | 0.000 | | | |
| Mg acetate•4H$_2$O | 0.357 | 214.46 | 0.0016 | 0.030 | | | |
| Zn Acetate | 0 | 183.46 | 0 | 0.000 | | | |
| Cyclohexylamine | 8.7495 | 99.17 | 0.0882 | 1.592 | | | |
| H$_2$O | 68 | 18 | 3.7777 | 68.150 | | | |

Example 5

Si$^{IV}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0 | 0.194024 | |
| H$_3$PO$_4$ (85%) | 5.392 | 97.93 | 0.0468 | 0.844 | 0% | 19% | 180 |
| Silica | 0.677 | 60.09 | 0.0112 | 0.203 | | | |
| Mg acetate•4H$_2$O | 0 | 214.46 | 0 | 0.000 | | | |
| Zn Acetate | 0 | 183.46 | 0 | 0.000 | | | |
| MDCHA | 8.7495 | 195.35 | 0.0447 | 0.808 | | | |
| H$_2$O | 76 | 18 | 4.2222 | 76.168 | | | |

Example 6

Zn$^{II}$Mg$^{II}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.0567 | 0 | |
| H$_3$PO$_4$ (85%) | 7.423 | 97.93 | 0.0644 | 1.162 | 5.7% | 0 | 190 |
| Silica | 0 | 60.09 | 0 | 0.000 | | | |

-continued

|  | Mass | RMM | Moles | Ratio | M Loading | Silica Loading | Temp (° C.) |
|---|---|---|---|---|---|---|---|
| Mg acetate•4H$_2$O | 0.357 | 214.46 | 0.0016 | 0.030 |  |  |  |
| Zn Acetate | 0.306 | 183.46 | 0.0016 | 0.030 |  |  |  |
| TPAOH | 8.7495 | 203.36 | 0.0430 | 0.776 |  |  |  |
| H$_2$O | 57 | 18 | 3.1666 | 57.126 |  |  |  |

Example 7

Mg$^{II}$Si$^{IV}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.02915 | 0.194024 |  |
| H$_3$PO$_4$ (85%) | 5.392 | 97.93 | 0.0468 | 0.844 | 2.9% | 19.4% | 180 |
| Silica | 0.677 | 60.09 | 0.0112 | 0.203 |  |  |  |
| Mg acetate•4H$_2$O | 0.357 | 214.46 | 0.0016 | 0.030 |  |  |  |
| Zn Acetate | 0 | 183.46 | 0 | 0.000 |  |  |  |
| MDCHA | 8.7495 | 195.35 | 0.0447 | 0.808 |  |  |  |
| H$_2$O | 65 | 18 | 3.6111 | 65.144 |  |  |  |

Example 8

Zn$^{II}$Si$^{IV}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.0292 | 0.175455 |  |
| H$_3$PO$_4$ (85%) | 6.1 | 97.93 | 0.0529 | 0.955 | 2.9% | 17.5% | 180 |
| Silica | 0.677 | 60.09 | 0.0112 | 0.203 |  |  |  |
| Mg acetate•4H$_2$O | 0 | 214.46 | 0 | 0.000 |  |  |  |
| Zn Acetate | 0.306 | 183.46 | 0.0016 | 0.030 |  |  |  |
| MDCHA | 8.7495 | 195.35 | 0.0447 | 0.808 |  |  |  |
| H$_2$O | 50 | 18 | 2.7777 | 50.111 |  |  |  |

Example 9

Mg$^{II}$Ti$^{IV}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.0567 | 0 |  |
| H$_3$PO$_4$ (85%) | 7.423 | 97.93 | 0.0644 | 1.162 | 5.7% | 0% | 200 |
| Silica | 0 | 60.09 | 0.0000 | 0.000 |  |  |  |
| Mg acetate•4H$_2$O | 0.357 | 214.46 | 0.0017 | 0.030 |  |  |  |
| Ti isopropoxide | 0.474 | 284.26 | 0.0017 | 0.030 |  |  |  |
| TPAOH | 8.7495 | 203.36 | 0.0430 | 0.776 |  |  |  |
| H$_2$O | 57 | 18 | 3.1667 | 57.126 |  |  |  |

Example 10

Zn$^{II}$Mg$^{II}$Si$^{IV}$AlPO-5

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.0567 | 0.177884 |  |
| H$_3$PO$_4$ (85%) | 5.999 | 97.93 | 0.0520 | 0.939 | 5.7% | 17.8% | 200 |
| Silica | 0.677 | 60.09 | 0.0112 | 0.203 |  |  |  |

-continued

|  | Mass | RMM | Moles | Ratio | M Loading | Silica Loading | Temp (° C.) |
|---|---|---|---|---|---|---|---|
| Mg acetate•4H$_2$O | 0.357 | 214.46 | 0.0016 | 0.030 | | | |
| Zn Acetate | 0.306 | 183.46 | 0.0016 | 0.030 | | | |
| MDCHA | 8.7495 | 195.35 | 0.0447 | 0.808 | | | |
| H$_2$O | 60 | 18 | 3.3333 | 60.133 | | | |

Example 11

Zn$^{II}$AlPO-18

|  | Mass | RMM | Moles | Ratio | M Loading | Silica Loading | Temp (° C.) |
|---|---|---|---|---|---|---|---|
| Al(OH)$_3$ | 4.22 | 77.95 | 0.0541 | 1.000 | 0.03130 | 0.0 | |
| H$_3$PO$_4$ (85%) | 6.35 | 97.93 | 0.0551 | 1.018 | 3.1% | 0.0% | 160 |
| Silica | 0 | 60.09 | 0 | 0.000 | | | |
| Mg acetate•4H$_2$O | 0 | 214.46 | 0 | 0.000 | | | |
| Zn Acetate | 0.321 | 183.46 | 0.0017 | 0.032 | | | |
| DIPE | 8.5 | 129.25 | 0.0657 | 1.215 | | | |
| H$_2$O | 65 | 18 | 3.6111 | 66.703 | | | |

Example 12

Mg$^{II}$AlPO-18

|  | Mass | RMM | Moles | Ratio | M Loading | Silica Loading | Temp (° C.) |
|---|---|---|---|---|---|---|---|
| Al(OH)$_3$ | 4.123 | 77.95 | 0.0528 | 1.000 | 0.0239 | 0 | |
| H$_3$PO$_4$ (85%) | 6.432 | 97.93 | 0.0558 | 1.055 | 2.4% | 0 | 150 |
| Silica | 0 | 60.09 | 0 | 0.000 | | | |
| Mg acetate•4H$_2$O | 3.572 | 214.46 | 0.0166 | 0.315 | | | |
| Zn Acetate | 0 | 183.46 | 0 | 0.000 | | | |
| DIPE | 8.7495 | 129.25 | 0.0676 | 1.280 | | | |
| H$_2$O | 70 | 18 | 3.8888 | 73.524 | | | |

Example 13

Si$^{IV}$AlPO-18

|  | Mass | RMM | Moles | Ratio | M Loading | Silica Loading | Temp (° C.) |
|---|---|---|---|---|---|---|---|
| Al(OH)$_3$ | 4.753 | 77.95 | 0.0609 | 1.000 | 0 | 0.202144 | |
| H$_3$PO$_4$ (85%) | 6.213 | 97.93 | 0.0539 | 0.884 | 0% | 20.2% | 170 |
| Silica | 0.821 | 60.09 | 0.0136 | 0.224 | | | |
| Mg acetate•4H$_2$O | 0 | 214.46 | 0 | 0.000 | | | |
| Zn Acetate | 0 | 183.46 | 0 | 0.000 | | | |
| DIPE | 8.7495 | 129.25 | 0.0676 | 1.110 | | | |
| H$_2$O | 65 | 18 | 3.6111 | 59.223 | | | |

Example 14

Zn$^{II}$Mg$^{II}$AlPO-18

|  | Mass | RMM | Moles | Ratio | M Loading | Silica Loading | Temp (° C.) |
|---|---|---|---|---|---|---|---|
| Al(OH)$_3$ | 4.652 | 77.95 | 0.0596 | 1.000 | 0.0586 | 0 | |
| H$_3$PO$_4$ (85%) | 7.345 | 97.93 | 0.0637 | 1.068 | 5.9% | 0 | 165 |

|  | Mass | RMM | Moles | Ratio | M Loading | Silica Loading | Temp (° C.) |
|---|---|---|---|---|---|---|---|
| Silica | 0 | 60.09 | 0 | 0.000 | | | |
| Mg acetate•4H$_2$O | 0.356 | 214.46 | 0.0016 | 0.028 | | | |
| Zn Acetate | 0.378 | 183.46 | 0.0020 | 0.035 | | | |
| TEA | 8.7495 | 101.07 | 0.0865 | 1.451 | | | |
| H$_2$O | 75 | 18 | 4.1666 | 69.818 | | | |

Example 15

Mg$^{II}$Si$^{IV}$AlPO-18

|  | Mass | RMM | Moles | Ratio | M Loading | Silica Loading | Temp (° C.) |
|---|---|---|---|---|---|---|---|
| Al(OH)$_3$ | 4.329 | 77.95 | 0.0555 | 1.000 | 0.0255 | 0.145633 | |
| H$_3$PO$_4$ (85%) | 7.345 | 97.93 | 0.0637 | 1.148 | 2.6% | 14.6% | 170 |
| Silica | 0.653 | 60.09 | 0.0108 | 0.196 | | | |
| Mg acetate•4H$_2$O | 0.312 | 214.46 | 0.0014 | 0.026 | | | |
| Zn Acetate | 0 | 183.46 | 0 | 0.000 | | | |
| DIPE | 8.7495 | 129.25 | 0.0676 | 1.219 | | | |
| H$_2$O | 66 | 18 | 3.6666 | 66.024 | | | |

Example 16

Zn$^{II}$Si$^{IV}$AlPO-18

|  | Mass | RMM | Moles | Ratio | M Loading | Silica Loading | Temp (° C.) |
|---|---|---|---|---|---|---|---|
| Al(OH)$_3$ | 4.229 | 77.95 | 0.0542 | 1.000 | 0.03724 | 0.193605 | |
| H$_3$PO$_4$ (85%) | 5.678 | 97.93 | 0.0492 | 0.908 | 3.7% | 19.4% | 170 |
| Silica | 0.711 | 60.09 | 0.0118 | 0.218 | | | |
| Mg acetate•4H$_2$O | 0 | 214.46 | 0 | 0.000 | | | |
| Zn Acetate | 0.385 | 183.46 | 0.0020 | 0.039 | | | |
| TEA | 8.7495 | 101.07 | 0.0865 | 1.596 | | | |
| H$_2$O | 68 | 18 | 3.7777 | 69.633 | | | |

Example 17

Zn$^{II}$Mg$^{II}$Si$^{IV}$AlPO-18

|  | Mass | RMM | Moles | Ratio | M Loading | Silica Loading | Temp (° C.) |
|---|---|---|---|---|---|---|---|
| Al(OH)$_3$ | 4.231 | 77.95 | 0.0542 | 1.000 | 0.0579 | 0.172101 | |
| H$_3$PO$_4$ (85%) | 6.567 | 97.93 | 0.0569 | 1.050 | 5.8% | 17.2% | 165 |
| Silica | 0.712 | 60.09 | 0.0118 | 0.218 | | | |
| Mg acetate•4H$_2$O | 0.367 | 214.46 | 0.0017 | 0.032 | | | |
| Zn Acetate | 0.299 | 183.46 | 0.0016 | 0.030 | | | |
| DIPE | 8.7495 | 129.25 | 0.0676 | 1.247 | | | |
| H$_2$O | 50 | 18 | 2.7777 | 51.177 | | | |

Example 18

Zn$^{II}$AlPO-34

|  | Mass | RMM | Moles | Ratio | M Loading | Silica Loading | Temp (° C.) |
|---|---|---|---|---|---|---|---|
| Al(OH)$_3$ | 4.111 | 77.95 | 0.0527 | 1.000 | 0.0377 | 0.0 | |
| H$_3$PO$_4$ (85%) | 6.935 | 97.93 | 0.0601 | 1.141 | 3.7% | 0.0% | 170 |
| Silica | 0 | 60.09 | 0 | 0.000 | | | |
| Mg acetate•4H$_2$O | 0 | 214.46 | 0 | 0.000 | | | |
| Zn Acetate | 0.38 | 183.46 | 0.0020 | 0.039 | | | |
| TEA | 8.5 | 101.07 | 0.0841 | 1.595 | | | |
| H$_2$O | 40 | 18 | 2.2222 | 42.136 | | | |

Example 19

Mg$^{II}$AlPO-34

|  | Mass | RMM | Moles | Ratio | M Loading | Silica Loading | Temp (° C.) |
|---|---|---|---|---|---|---|---|
| Al(OH)$_3$ | 4.222 | 77.95 | 0.0541 | 1.000 | 0.0315 | 0 | |
| H$_3$PO$_4$ (85%) | 7.113 | 97.93 | 0.0617 | 1.140 | 3.2% | 0 | 170 |
| Silica | 0 | 60.09 | 0 | 0.000 | | | |
| Mg acetate•4H$_2$O | 0.378 | 214.46 | 0.0017 | 0.033 | | | |
| Zn Acetate | 0 | 183.46 | 0 | 0.000 | | | |
| TEA | 8.7495 | 101.07 | 0.0865 | 1.598 | | | |
| H$_2$O | 45 | 18 | 2.5 | 46.157 | | | |

Example 20

Si$^{IV}$AlPO-34

|  | Mass | RMM | Moles | Ratio | M Loading | Silica Loading | Temp (° C.) |
|---|---|---|---|---|---|---|---|
| Al(OH)$_3$ | 4.234 | 77.95 | 0.0543 | 1.000 | 0 | 0.211847 | |
| H$_3$PO$_4$ (85%) | 5.892 | 97.93 | 0.0511 | 0.942 | 0% | 21.2% | 160 |
| Silica | 0.826 | 60.09 | 0.0137 | 0.253 | | | |
| Mg acetate•4H$_2$O | 0 | 214.46 | 0 | 0.000 | | | |
| Zn Acetate | 0 | 183.46 | 0 | 0.000 | | | |
| MOR | 8.7495 | 87.12 | 0.1004 | 1.849 | | | |
| H$_2$O | 35 | 18 | 1.9444 | 35.798 | | | |

Example 21

Zn$^{II}$Mg$^{II}$AlPO-34

|  | Mass | RMM | Moles | Ratio | M Loading | Silica Loading | Temp (° C.) |
|---|---|---|---|---|---|---|---|
| Al(OH)$_3$ | 3.911 | 77.95 | 0.0501 | 1.000 | 0.0691 | 0 | |
| H$_3$PO$_4$ (85%) | 5.974 | 97.93 | 0.0518 | 1.033 | 6.9% | 0 | 180 |
| Silica | 0 | 60.09 | 0 | 0.000 | | | |
| Mg acetate•4H$_2$O | 0.345 | 214.46 | 0.0016 | 0.032 | | | |
| Zn Acetate | 0.389 | 183.46 | 0.0021 | 0.042 | | | |
| TEA | 8.7495 | 101.07 | 0.0865 | 1.725 | | | |
| H$_2$O | 45 | 18 | 2.5 | 49.827 | | | |

Example 22

$Mg^{II}Si^{IV}AlPO-34$

| | Mass | RMM | Moles | Ratio | M Loading | Silica Loading | Temp (° C.) |
|---|---|---|---|---|---|---|---|
| Al(OH)$_3$ | 4.012 | 77.95 | 0.0514 | 1.000 | 0.0303 | 0.201621 | |
| H$_3$PO$_4$ (85%) | 5.231 | 97.93 | 0.0454 | 0.882 | 3.0% | 20.2% | 170 |
| Silica | 0.689 | 60.09 | 0.0114 | 0.223 | | | |
| Mg acetate•4H$_2$O | 0.345 | 214.46 | 0.0016 | 0.031 | | | |
| Zn Acetate | 0 | 183.46 | 0 | 0.000 | | | |
| MOR | 8.7495 | 87.12 | 0.1004 | 1.951 | | | |
| H$_2$O | 56 | 18 | 3.1111 | 60.446 | | | |

Example 23

$Zn^{II}Si^{IV}AlPO-34$

| | Mass | RMM | Moles | Ratio | M Loading | Silica Loading | Temp (° C.) |
|---|---|---|---|---|---|---|---|
| Al(OH)$_3$ | 3.92 | 77.95 | 0.0502 | 1.000 | 0.0327 | 0.208683 | |
| H$_3$PO$_4$ (85%) | 5.351 | 97.93 | 0.0464 | 0.924 | 3.3% | 20.9% | 160 |
| Silica | 0.736 | 60.09 | 0.0122 | 0.244 | | | |
| Mg acetate•4H$_2$O | 0 | 214.46 | 0 | 0.000 | | | |
| Zn Acetate | 0.312 | 183.46 | 0.0017 | 0.034 | | | |
| TEAOH | 8.7495 | 147.27 | 0.0594 | 1.181 | | | |
| H$_2$O | 60 | 18 | 3.3333 | 66.284 | | | |

Example 24

$Zn^{II}Mg^{II}Si^{IV}AlPO-34$

| | Mass | RMM | Moles | Ratio | M Loading | Silica Loading | Temp (° C.) |
|---|---|---|---|---|---|---|---|
| Al(OH)$_3$ | 4.502 | 77.95 | 0.0577 | 1.000 | 0.0460 | 0.177342 | |
| H$_3$PO$_4$ (85%) | 5.541 | 97.93 | 0.0480 | 0.833 | 4.6% | 17.7% | 160 |
| Silica | 0.623 | 60.09 | 0.0103 | 0.180 | | | |
| Mg acetate•4H$_2$O | 0.299 | 214.46 | 0.0013 | 0.024 | | | |
| Zn Acetate | 0.256 | 183.46 | 0.0013 | 0.024 | | | |
| MOR | 8.7495 | 87.12 | 0.1004 | 1.739 | | | |
| H$_2$O | 60 | 18 | 3.3333 | 57.715 | | | |

Example 25

$Zn^{II}AlPO-36$

| | Mass | RMM | Moles | Ratio | M Loading | Silica Loading | Temp (° C.) |
|---|---|---|---|---|---|---|---|
| Al(OH)$_3$ | 4.322 | 77.95 | 0.0554 | 1.000 | 0.0368 | 0.0 | |
| H$_3$PO$_4$ (85%) | 5.472 | 97.93 | 0.0474 | 0.857 | 3.7% | 0.0% | 190 |
| Silica | 0 | 60.09 | 0 | 0.000 | | | |
| Mg acetate•4H$_2$O | 0 | 214.46 | 0 | 0.000 | | | |
| Zn Acetate | 0.389 | 183.46 | 0.0021 | 0.038 | | | |
| EDCHA | 8.5 | 209.37 | 0.0405 | 0.732 | | | |
| H$_2$O | 50 | 18 | 2.7777 | 50.099 | | | |

Example 26

$Mg^{II}AlPO-36$

|  | Mass | RMM | Moles | Ratio | M Loading | Silica Loading | Temp (° C.) |
|---|---|---|---|---|---|---|---|
| Al(OH)$_3$ | 4.444 | 77.95 | 0.0570 | 1.000 | 0.0311 | 0 |  |
| H$_3$PO$_4$ (85%) | 6.689 | 97.93 | 0.0580 | 1.018 | 3.1% | 0 | 200 |
| Silica | 0 | 60.09 | 0 | 0.000 |  |  |  |
| Mg acetate•4H$_2$O | 0.393 | 214.46 | 0.0018 | 0.032 |  |  |  |
| Zn Acetate | 0 | 183.46 | 0 | 0.000 |  |  |  |
| EDCHA | 8.7495 | 209.37 | 0.0417 | 0.733 |  |  |  |
| H$_2$O | 56 | 18 | 3.1111 | 54.570 |  |  |  |

Example 27

$Si^{IV}AlPO-36$

|  | Mass | RMM | Moles | Ratio | M Loading | Silica Loading | Temp (° C.) |
|---|---|---|---|---|---|---|---|
| Al(OH)$_3$ | 4.201 | 77.95 | 0.0538 | 1.000 | 0 | 0.243034 |  |
| H$_3$PO$_4$ (85%) | 5.5 | 97.93 | 0.0477 | 0.886 | 0% | 24.3% | 180 |
| Silica | 0.921 | 60.09 | 0.0153 | 0.284 |  |  |  |
| Mg acetate•4H$_2$O | 0 | 214.46 | 0 | 0.000 |  |  |  |
| Zn Acetate | 0 | 183.46 | 0 | 0.000 |  |  |  |
| EDCHA | 8.7495 | 209.37 | 0.0417 | 0.775 |  |  |  |
| H$_2$O | 80 | 18 | 4.4444 | 82.467 |  |  |  |

Example 28

$Zn^{II}Mg^{II}AlPO-36$

|  | Mass | RMM | Moles | Ratio | M Loading | Silica Loading | Temp (° C.) |
|---|---|---|---|---|---|---|---|
| Al(OH)$_3$ | 3.901 | 77.95 | 0.0500 | 1.000 | 0.0637 | 0 |  |
| H$_3$PO$_4$ (85%) | 7.543 | 97.93 | 0.0654 | 1.308 | 6.4% | 0 | 190 |
| Silica | 0 | 60.09 | 0 | 0.000 |  |  |  |
| Mg acetate•4H$_2$O | 0.367 | 214.46 | 0.0017 | 0.034 |  |  |  |
| Zn Acetate | 0.311 | 183.46 | 0.0016 | 0.034 |  |  |  |
| EDCHA | 8.7495 | 209.37 | 0.0417 | 0.835 |  |  |  |
| H$_2$O | 70 | 18 | 3.8888 | 77.708 |  |  |  |

Example 29

$Mg^{II}Si^{IV}AlPO-36$   50

|  | Mass | RMM | Moles | Ratio | M Loading | Silica Loading | Temp (° C.) |
|---|---|---|---|---|---|---|---|
| Al(OH)$_3$ | 4.342 | 77.95 | 0.0557 | 1.000 | 0.0246 | 0.138867 |  |
| H$_3$PO$_4$ (85%) | 6.456 | 97.93 | 0.0560 | 1.006 | 2.5% | 13.9% | 190 |
| Silica | 0.543 | 60.09 | 0.0090 | 0.162 |  |  |  |
| Mg acetate•4H$_2$O | 0.302 | 214.46 | 0.0014 | 0.025 |  |  |  |
| Zn Acetate | 0 | 183.46 | 0 | 0.000 |  |  |  |
| TPA | 8.7495 | 143.27 | 0.0610 | 1.096 |  |  |  |
| H$_2$O | 65 | 18 | 3.6111 | 64.829 |  |  |  |

Example 30

$Zn^{II}Si^{IV}AlPO$-36

|  | Mass | RMM | Moles | Ratio | M Loading | Silica Loading | Temp (° C.) |
|---|---|---|---|---|---|---|---|
| Al(OH)$_3$ | 4.321 | 77.95 | 0.0554 | 1.000 | 0.0284 | 0.1549723 |  |
| H$_3$PO$_4$ (85%) | 6.231 | 97.93 | 0.0540 | 0.976 | 2.8% | 15.5% | 200 |
| Silica | 0.596 | 60.09 | 0.0099 | 0.179 |  |  |  |
| Mg acetate•4H$_2$O | 0 | 214.46 | 0 | 0.000 |  |  |  |
| Zn Acetate | 0.298 | 183.46 | 0.0016 | 0.029 |  |  |  |
| TPA | 8.7495 | 143.27 | 0.0610 | 1.102 |  |  |  |
| H$_2$O | 70 | 18 | 3.8888 | 70.155 |  |  |  |

Example 31

$Zn^{II}Mg^{II}Si^{IV}AlPO$-36

|  | Mass | RMM | Moles | Ratio | M Loading | Silica Loading | Temp (° C.) |
|---|---|---|---|---|---|---|---|
| Al(OH)$_3$ | 4.229 | 77.95 | 0.0542 | 1.000 | 0.0617 | 0.1411797 |  |
| H$_3$PO$_4$ (85%) | 5.925 | 97.93 | 0.0514 | 0.948 | 6.2% | 14.1% | 190 |
| Silica | 0.508 | 60.09 | 0.0084 | 0.156 |  |  |  |
| Mg acetate•4H$_2$O | 0.311 | 214.46 | 0.0014 | 0.027 |  |  |  |
| Zn Acetate | 0.389 | 183.46 | 0.0021 | 0.039 |  |  |  |
| EDCHA | 8.7495 | 209.37 | 0.0417 | 0.770 |  |  |  |
| H$_2$O | 57 | 18 | 3.1666 | 58.369 |  |  |  |

Example 32

Phase Purity

Figure 2:
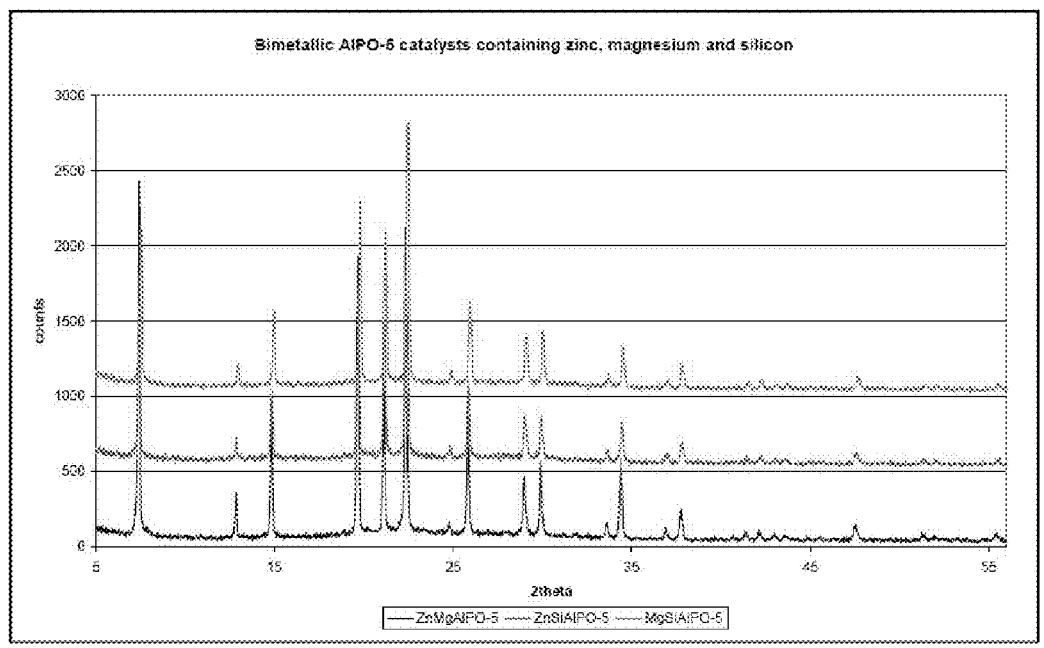
FIG. 2 is an X-ray Diffraction Pattern of 3 different isomorphously multiply substituted bi-metallic AlPO-5s ($Zn^{II}Mg^{II}$, $Zn^{II}Si^{IV}$, and $Mg^{II}Si^{IV}$) showing they are phase pure and crystalline.
Figure 3:
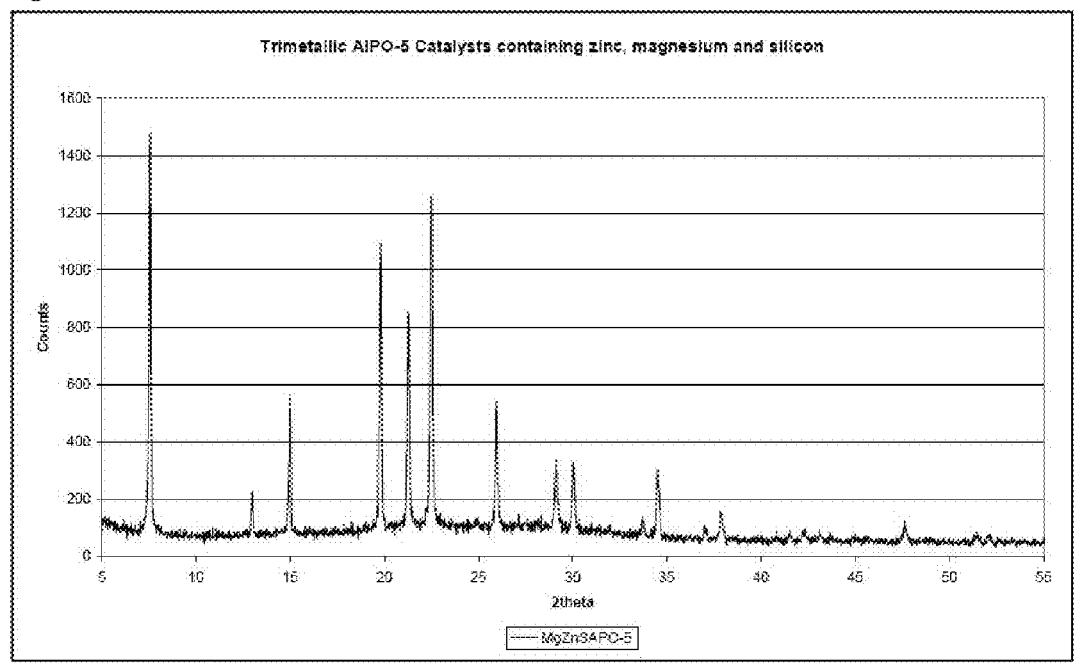
FIG. 3 is an X-ray Diffraction Pattern of an isomorphously multiply substituted bi-metallic AlPO-5 ($Mg^{II}Zn^{II}Si^{IV}$) showing it is phase pure and crystalline.
Figure 4:
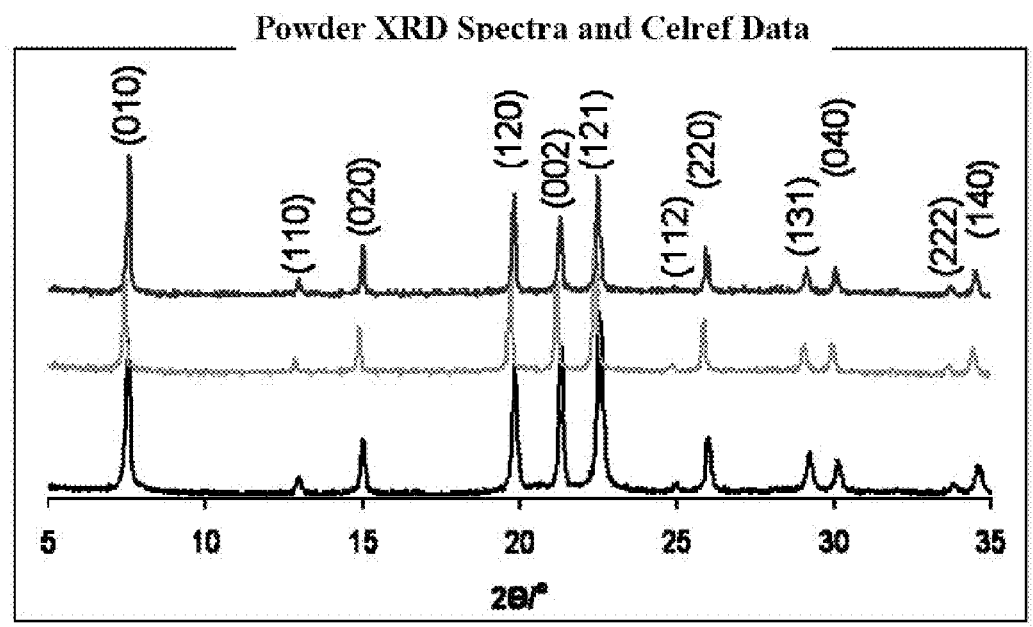
FIG. 4 is the Celref analysis of the XRD traces in FIGS. 1-3 showing the correlation between observed and theoretically calculated peaks are only different on average by less than 0.1000°.

In FIGS. 1 through 3, the XRD patterns of the mono- and bi-metallic substituted AlPOs of this invention are shown, respectively. The patterns were compared with the AFI reported powder pattern from the IZA website (FIG. 5(A)) and various published reports. The FIGS. 1 through 3 show that a very high level of AFI structure phase purity and crystallinity is achieved even after metal substitution. The Celref analysis in FIG. 4 also shows an almost perfect correlation between observed and theoretically calculated peaks. In most cases, a difference in 2theta of less than 0.1000° was observed. Similar analysis was performed on the $Mg^{II}Zn^{II}Si^{IV}AlPO$-5 catalysts also showing a strong correlation between the calculated and observed peaks. Again, in almost all cases, differences of 2theta were smaller than 0.1000° as shown below in Table 2.

TABLE 2

Refined Final Values for $Mg^{II}Zn^{II}Si^{IV}AlPO$-5

| Lambda | a | b | c | alpha | beta | gamma | volume |
|---|---|---|---|---|---|---|---|
| 1.54000 | 13.6900 | 13.6900 | 8.4730 | 90.00 | 90.00 | 120.00 | 1375.22 |

| h | k | l | 2Theta (observed) | 2Theta (calculated) | Difference |
|---|---|---|---|---|---|
| 0 | 1 | 0 | 7.54 | 7.4476 | 0.0924 |
| 1 | 1 | 0 | 12.98 | 12.9179 | 0.0621 |
| 0 | 2 | 0 | 14.94 | 14.9269 | 0.0131 |
| 1 | 2 | 0 | 19.84 | 19.7888 | 0.0512 |
| 0 | 3 | 0 | 22.52 | 22.4708 | 0.0492 |
| 1 | 1 | 2 | 24.76 | 24.7342 | 0.0258 |
| 2 | 2 | 0 | 25.98 | 26.0037 | −0.0237 |
| 1 | 3 | 1 | 29.14 | 29.0953 | 0.0447 |

TABLE 2-continued

Refined Final Values for $Mg^{II}Zn^{II}Si^{IV}AlPO$-5

| 0 | 4 | 0 | 30.08 | 30.1149 | −0.0349 |
|---|---|---|---|---|---|
| 2 | 2 | 2 | 33.78 | 33.6833 | 0.0967 |
| 1 | 4 | 0 | 34.54 | 34.6298 | −0.0898 |
| 0 | 4 | 2 | 37.04 | 36.9699 | 0.0701 |
| 0 | 5 | 0 | 37.86 | 37.8989 | −0.0389 |
| 2 | 4 | 1 | 41.68 | 41.6456 | 0.0344 |
| 1 | 5 | 0 | 42.36 | 42.3980 | −0.0380 |
| 0 | 1 | 4 | 43.24 | 43.3407 | −0.1007 |
| 1 | 5 | 1 | 43.90 | 43.7833 | 0.1167 |
| 2 | 5 | 0 | 47.80 | 47.8565 | −0.0565 |
| 1 | 6 | 1 | 51.64 | 51.6307 | 0.0093 |
| 2 | 5 | 2 | 52.80 | 52.7769 | 0.0231 |
| 2 | 6 | 0 | 55.70 | 55.8529 | −0.1529 |

Example 33

Metal-substituted catalysts of the invention prepared according to the general procedure described above, as exemplified in Examples 1 through 31, were evaluated as follows in the liquid phase:

The catalytic reactions were carried out in a stainless-steel high-pressure 0.1 liter Parr 4590 catalytic reactor lined with Poly Ether Ether Ketone (PEEK) that uses a 4843 Parr controller. The substrate (typically 10 g), a suitable internal standard (tetralin; 50 mg), and the isomorphously metal-substituted AlPO catalyst (0.2 g, calcined at 823 K for 8 h prior to the catalytic tests), were introduced into the reactor, which was subsequently sealed. The reactor and the inlet and outlet ports were purged three times with dry nitrogen prior to reaction. The contents were stirred at 1200 rpm and the reactor was heated to the desired temperature under autogeneous pressure (N$_2$). Optionally, the contents of the reactor can be pressurized to several bar of $N_2$ (<60 bar), in order to keep the contents in the liquid-phase and minimize gas-phase reactions.

At the end of the reaction, the heating was turned off and the contents of the reactor were cooled (quenched) to 290 K. A mass-balance calculation was performed at this stage to check for handling and mass losses. Where kinetic and rate effects were studied, a mini-robot liquid sampling valve was employed to remove small aliquots (0.1 µl) of the sample during the course of the reaction. These data are displayed in the kinetic traces of FIGS. 5 through 8. The products were analyzed either online (using a robotically-controlled unit with an online computer-controlled system which is linked to a GC and/or LCMS) or offline by a Varian Star 3400CX gas chromatograph employing a HP-1 capillary column cross-linked with methylsiloxane (30 m×0.32 mm×1 µm film thickness) and a flame ionization detector using a variable ramp temperature program (from 40° C. to 200° C.). The identities of the products were confirmed using authenticated standards and their individual response factors were determined using the internal standard calibration method. The overall yields were normalized with respect to the (GC) response factors obtained as above and the conversions and selectivities were determined by the following equations:

Conv. %=[(moles of initial substrate−moles of residual substrate)/(moles of initial substrate)]× 100 Sel.=[(moles of individual product)/(moles of total products)]×100

For the internal standard GC method, the response factor (RF) and mol % of individual products were calculated using the following equations:

RF=(mol Product/mol Standard)×(Area Standard/Area Product) Mol % Product=RF×Mol Standard× (Area Product/Area Standard)×100/Mol Sample

TABLE 3

Efficacy of Multi-Substituted Brönsted-Acid Sites for the Catalytic Dehydration of Ethanol

| Catalyst | Temperature (K) | TOF ($h^{-1}$) | Total Conversion (mol. %) | Ethylene Conv. (mol. %) |
|---|---|---|---|---|
| $Mg^{II}Si^{IV}$AlPO-5 | 453 | 656 | 78.5 | 88 |
| $Zn^{II}Si^{IV}$AlPO-18 | 463 | 575 | 72.8 | 92 |
| $Zn^{II}Si^{IV}$AlPO-5 | 453 | 680 | 80.7 | 89 |
| $Zn^{II}Ti^{IV}$AlPO-18 | 453 | 466 | 61.2 | 88 |
| $Mg^{II}Si^{IV}Zn^{II}$AlPO-5 | 423 | 700 | 75.7 | 98 |
| $Mg^{II}Ti^{IV}$AlPO-36 | 433 | 415 | 51.2 | 82 |
| $Mg^{II}Si^{IV}$AlPO-18 | 443 | 578 | 78.8 | 91 |
| $Mg^{II}Ti^{IV}$AlPO-5 | 453 | 527 | 60.0 | 85 |
| $Zn^{II}Si^{IV}$AlPO-5 | 353 | 65 | 9.5 | 99+ |
| $Zn^{II}Ti^{IV}$AlPO-36 | 443 | 500 | 61.2 | 88 |
| $Mg^{II}Si^{IV}$AlPO-34 | 433 | 691 | 81.3 | 93 |
| $Mg^{II}Si^{IV}$AlPO-18 | 353 | 38 | 5.0 | 98 |
| $Mg^{II}Si^{IV}$AlPO-5 | 423 | 712 | 70.0 | 96 |

TABLE 4

Efficacy of Single-Substituted Brönsted-Acid Sites for the Catalytic Dehydration of Ethanol

| Catalyst | Temperature (K) | TOF ($h^{-1}$) | Total Conversion (mol. %) | Ethylene Conv. (mol. %) |
|---|---|---|---|---|
| $Si^{IV}$AlPO-5 | 453 | 420 | 48.0 | 92 |
| $Ti^{IV}$AlPO-36 | 433 | 305 | 41.2 | 76 |
| $Ti^{IV}$AlPO-5 | 453 | 345 | 40.0 | 75 |
| $Si^{IV}$AlPO-34 | 453 | 480 | 53.7 | 96 |
| $Si^{IV}$AlPO-18 | 463 | 545 | 58.8 | 97 |
| $Ti^{IV}$AlPO-36 | 443 | 290 | 35.3 | 65 |
| $Si^{IV}$AlPO-5 | 353 | 51 | 8.0 | 99+ |
| $Si^{IV}$AlPO-18 | 353 | 35 | 4.2 | 97 |
| $Ti^{IV}$AlPO-18 | 453 | 310 | 41.2 | 68 |
| $Ti^{IV}$AlPO-34 | 443 | 345 | 45.0 | 66 |
| $Si^{IV}$AlPO-5 | 453 | 413 | 55.7 | 91 |
| $Si^{IV}$AlPO-18 | 443 | 480 | 51.8 | 98 |
| $Si^{IV}$AlPO-36 | 453 | 486 | 59.5 | 90 |
| $Mg^{II}$AlPO-5 | 463 | 466 | 61.5 | 96 |
| $Zn^{II}$AlPO-18 | 473 | 515 | 63.2 | 99+ |
| $Mg^{II}$AlPO-36 | 473 | 385 | 68.2 | 95 |
| $Mg^{II}$AlPO-34 | 353 | 21 | 3.3 | 92 |
| $Zn^{II}$AlPO-5 | 483 | 500 | 70.7 | 94 |
| $Mg^{II}$AlPO-34 | 453 | 491 | 66.3 | 99+ |
| $Zn^{II}$AlPO-36 | 463 | 566 | 61.7 | 95 |
| $Mg^{II}$AlPO-18 | 443 | 499 | 58.8 | 99+ |
| $Mg^{II}$AlPO-5 | 353 | 56 | 6.5 | 99+ |

Example 34

Metal-substituted catalysts of the invention prepared according to the general procedure described above, as exemplified in Examples 8, were evaluated by the general procedure above, as exemplified in Example 33, in the liquid phase:

TABLE 5

Efficacy of Multi-Substituted Brönsted-Acid Sites for the Catalytic Dehydration of Propanol

| Catalyst | Temperature (K) | Total Conversion (mol. %) | Propylene Conv. (mol. %) |
|---|---|---|---|
| $Mg^{II}Si^{IV}Zn^{II}$AlPO-5 | 423 | 74.0 | 93 |

The claimed invention is:

1. A substantially phase pure, calcined aluminophosphate, $AlPO_4$, wherein at least one aluminum ($Al^{III}$) site is isomorphously metal-substituted by a divalent metal ion ($M^{II}$) or at least one phosphorous ($P^V$) site is isomorphously metal-substituted by a tetravalent metal ion ($M^{IV}$).

2. An aluminophosphate of claim 1, wherein the divalent metal ion is selected from the group consisting of $Zn^{II}$, $Mg^{II}$, $Co^{II}$, $Ca^{II}$, $Ni^{II}$, $Pd^{II}$, and mixtures thereof and the tetravalent metal ion is selected from the group consisting of $Si^{IV}$, $Zr^{IV}$, $Pt^{IV}$, $Sn^{IV}$, $Ti^{IV}$, $Ge^{IV}$, $Pd^{IV}$, a and mixtures thereof.

3. An aluminophosphate of claim 2, wherein the molar amount of $M^{II}$ substituted for $Al^{III}$ ranges from about 0.001 to about 0.10 moles $M^{II}$ and the molar amount of $M^{IV}$ substituted for $P^V$ ranges from about 0.01 to about 0.25 moles $M^{IV}$.

4. An aluminophosphate of claim 1 having a pore size ranging from about 3 Ångstroms to about 15 Ångstroms.

5. An aluminophosphate of claim 1 wherein the aluminophosphate has an AlPO-5 framework, an AlPO-18 framework, an AlPO-34 framework, or an AlPO-36 framework.

6. An aluminophosphate of claim 2 selected from the group consisting of $Mg^{II}Si^{IV}$ AlPO-5, $Zn^{II}Si^{IV}$AlPO-18, $Zn^{II}Si^{IV}$AlPO-5, $Zn^{II}Ti^{IV}$AlPO-18, $Mg^{II}Si^{IV}Zn^{II}$AlPO-5, $Mg^{II}Ti^{IV}$AlPO-36, $Mg^{II}Si^{IV}$AlPO-18, $Mg^{II}Ti^{IV}$AlPO-5, $Zn^{II}Si^{IV}AlPO-5$, $Zn^{II}Ti^{IV}AlPO-36$, $Mg^{II}Si^{IV}AlPO-34$, $Mg^{II}Si^{IV}AlPO-18$, and $Mg^{II}Si^{IV}AlPO-5$.

7. An aluminophosphate of claim 2 selected from the group consisting of $Si^{IV}AlPO-5$, $Ti^{IV}AlPO-36$, $Ti^{IV}AlPO-5$, $Si^{IV}AlPO-34$, $Si^{IV}AlPO-18$, $Ti^{IV}AlPO-36$, $Si^{IV}AlPO-5$, $Si^{IV}AlPO-18$, $Ti^{IV}AlPO-18$, $Ti^{IV}AlPO-34$, $Si^{IV}AlPO-5$, $Si^{IV}AlPO-18$, $Si^{IV}AlPO-36$, $Mg^{II}AlPO-5$, $Zn^{II}AlPO-18$, $Mg^{II}AlPO-36$, $Mg^{II}AlPO-34$, $Zn^{II}AlPO-5$, $Mg^{II}AlPO-34$, $Zn^{II}AlPO-36$, $Mg^{II}AlPO-18$, and $Mg^{II}AlPO-5$.

8. The substantially pure, calcined aluminophosphate of claim 1 having an X-ray diffraction pattern with an observed 2Theta position for each peak that is less than 0.1000° different from a respective calculated 2Theta position for each said peak.

9. A substantially phase pure, calcined aluminophosphate, $AlPO_4$, wherein at least one aluminum ($Al^{III}$) site is isomorphously metal-substituted by a divalent metal ion ($M^{II}$) and at least one phosphorous ($P^V$) site is isomorphously metal-substituted by a tetravalent metal ion ($M^{IV}$).

10. An aluminophosphate of claim 9, wherein the divalent metal ion is selected from the group consisting of $Zn^{II}$, $Mg^{II}$, $Co^{II}$, $Ca^{II}$, $Ni^{II}$, $Pd^{II}$, and mixtures thereof and the tetravalent metal ion is selected from the group consisting of $Si^{IV}$, $Zr^{IV}$, $Pt^{IV}$, $Sn^{IV}$, $Ti^{IV}$, $Ge^{IV}$, $Pd^{IV}$, and mixtures thereof.

11. An aluminophosphate of claim 10, wherein the molar amount of $M^{II}$ substituted for $Al^{III}$ ranges from about 0.001 to about 0.10 moles $M^{II}$ and the molar amount of $M^{IV}$ substituted for $P^V$ ranges from about 0.01 to about 0.25 moles $M^{IV}$.

12. An aluminophosphate of claim 9 having a pore size ranging from about 3 Ångstroms to about 15 Ångstroms.

13. An aluminophosphate of claim 9 wherein the aluminophosphate has an AlPO-5 framework, an AlPO-18 framework, an AlPO-34 framework, or an AlPO-36 framework.

14. An aluminophosphate of claim 10 selected from the group consisting of $Mg^{II}Si^{IV}AlPO-5$, $Zn^{II}Si^{IV}AlPO-18$, $Zn^{II}Si^{IV}AlPO-5$, $Zn^{II}Ti^{IV}AlPO-18$, $Mg^{II}Si^{IV}Zn^{II}AlPO-5$, $Mg^{II}Ti^{IV}AlPO-36$, $Mg^{II}Si^{IV}AlPO-18$, $Mg^{II}Ti^{IV}AlPO-5$, $Zn^{II}Si^{IV}AlPO-5$, $Zn^{II}Ti^{IV}AlPO-36$, $Mg^{II}Si^{IV}AlPO-34$, $Mg^{II}Si^{IV}AlPO-18$, and $Mg^{II}Si^{IV}AlPO-5$.

15. An aluminophosphate of claim 10 selected from the group consisting of $Si^{IV}AlPO-5$, $Ti^{IV}AlPO-36$, $Ti^{IV}AlPO-5$, $Si^{IV}AlPO-34$, $Si^{IV}AlPO-18$, $Ti^{IV}AlPO-36$, $Si^{IV}AlPO-5$, $Si^{IV}AlPO-18$, $Ti^{IV}AlPO-18$, $Ti^{IV}AlPO-34$, $Si^{IV}AlPO-5$, $Si^{IV}AlPO-18$, $Si^{IV}AlPO-36$, $Mg^{II}AlPO-5$, $Zn^{II}AlPO-18$, $Mg^{II}AlPO-36$, $Mg^{II}AlPO-34$, $Zn^{II}AlPO-5$, $Mg^{II}AlPO-34$, $Zn^{II}AlPO-36$, $Mg^{II}AlPO-18$, and $Mg^{II}AlPO-5$.

16. The substantially pure, calcined aluminophosphate of claim 9 having an X-ray diffraction pattern with an observed 2Theta position for each peak that is less than 0.1000° different from a respective calculated 2Theta position for each said peak.

17. A process for the dehydration of alcohols to form olefins, comprising the step of:
contacting a feedstock containing an alcohol with an aluminophosphate of claim 1 or 9 under conditions sufficient to convert the alcohol to an olefin.

18. A process of claim 17, wherein the alcohol is a $C_2$-$C_{10}$ alcohol.

19. A process of claim 17, wherein the feedstock is contacted with the aluminophosphate at a temperature ranging between about 23° C. and about 700° C.

20. A process of claim 17, wherein the feedstock is contacted with the aluminophosphate at a temperature ranging between about 50° C. and about 250° C. and at a pressure of 1 atmosphere to 30 atmospheres.

21. A process of claim 19, wherein the alcohol is a liquid.

22. A process of claim 21, wherein ethanol is converted to ethylene, propanol is converted to propylene, t-butyl alcohol is converted to isobutylene, or methyl benzyl alcohol is converted to styrene.

23. A process for preparing a substantially phase pure, calcined metal-substituted aluminophosphate, AlPO, wherein at least one aluminum ($Al^{III}$) site is substituted by a divalent metal ion ($M^{II}$) and/or at least one phosphorous ($P^V$) site is substituted by a tetravalent metal ion ($M^{IV}$), comprising the steps of:
adding a phosphorous source to water to form an aqueous mixture,
stirring the aqueous mixture,
adding an aluminum source to the stirred aqueous mixture to form a first reaction mixture,
adding at least one aqueous solution or suspension of a $M^{II}$ metal source, $M^{IV}$ metal source, or both to the stirred first reaction mixture,
stirring the first reaction mixture containing the metal source for a time sufficient to form a homogenized mixture,
optionally adding a further quantity of water to the stirred homogenized mixture,
adding a structure directing agent to the stirred homogenized mixture to form a second reaction mixture,
optionally adding water,
stirring the second reaction mixture until the reaction is complete to form a substituted AlPO reaction product mixture,
aging the substituted AlPO reaction product mixture,
autoclaving the aged substituted AlPO reaction product mixture in a high pressure autoclave unit equipped with resistant liners at a temperature ranging between about 23° C. and about 500° C. for up to about 6 hours,
quenching the autoclave,
filtering the autoclaved substituted AlPO reaction product mixture to recover a solid catalyst product,
washing the solid catalyst product with water,
drying the solid catalyst product,
slowly heating the dried catalyst product under a flowing inert gas at a calcination temperature ranging between about 200° C. and about 1000° C.,
holding the dried catalyst product under the flowing inert gas at the calcinations temperature,
calcining the dried catalyst product for a time of at least about 3 to about 24 hours to form a substantially phase pure, calcined metal-substituted aluminophosphate, and
slowly cooling the substantially phase pure, calcined metal-substituted aluminophosphate to room temperature.

24. A process of claim 23, wherein the inert gas is nitrogen and the calcining step comprises calcining under a flow of dry air.

25. A process for preparing a substantially phase pure, calcined metal-substituted aluminophosphate, AlPO, wherein at least one aluminum ($Al^{III}$) site is substituted by a divalent metal ion ($M^{II}$) and/or at least one phosphorous ($P^V$) site is substituted by a tetravalent metal ion ($M^{IV}$) comprising the steps of:
slowly heating an isomorphously, metal-substituted aluminophosphate catalyst product containing a structure directing agent within its crystalline structure under a flowing inert gas at a calcination temperature ranging between about 200° C. and about 1000° C.,
holding the isomorphously, metal-substituted aluminophosphate catalyst product under the flowing inert gas at the calcination temperature, calcining the isomorphously, metal-substituted aluminophosphate catalyst product for a time of at least about 3 to about 24 hours to form a substantially phase pure, calcined metal-substituted aluminophosphate, and slowly cooling the substantially phase pure, calcined metal-substituted aluminophosphate to room temperature.

26. A process of claim 25, wherein the inert gas is nitrogen and the calcining step comprises calcining under a flow of dry air.

* * * * *